(12) United States Patent
Frank et al.

(10) Patent No.: US 8,580,953 B2
(45) Date of Patent: *Nov. 12, 2013

(54) WATER-ABSORBING POLYSACCHARIDE AND METHOD FOR PRODUCING THE SAME

(75) Inventors: Markus Frank, Baden-Baden (DE); Frank Loeker, Krefeld (DE); Dirk Paepen, Geldem (DE); Scott Smith, Greensboro, NC (US)

(73) Assignee: Evonik Degussa GmbH, Essen (DE)

( * ) Notice: Subject to any disclaimer, the term of this patent is extended or adjusted under 35 U.S.C. 154(b) by 1160 days.

This patent is subject to a terminal disclaimer.

(21) Appl. No.: 11/570,849

(22) PCT Filed: Jun. 20, 2005

(86) PCT No.: PCT/EP2005/006619
§ 371 (c)(1),
(2), (4) Date: Aug. 6, 2007

(87) PCT Pub. No.: WO2005/123781
PCT Pub. Date: Dec. 29, 2005

(65) Prior Publication Data
US 2008/0009616 A1    Jan. 10, 2008

(30) Foreign Application Priority Data

Jun. 21, 2004 (DE) .................. 10 2004 029 713
Jun. 22, 2004 (DE) .................. 10 2004 030 182
Mar. 24, 2005 (DE) .................. 10 2005 013 893

(51) Int. Cl.
*C08B 15/00* (2006.01)

(52) U.S. Cl.
USPC ..................................... 536/123.1

(58) Field of Classification Search
USPC ..................................... 536/123.1
See application file for complete search history.

(56) References Cited

U.S. PATENT DOCUMENTS

| | | | |
|---|---|---|---|
| 3,555,009 A | 1/1971 | Suzuki et al. | |
| 3,658,790 A | 4/1972 | Bemardin | |
| 4,075,279 A | 2/1978 | Holst et al. | |
| 4,952,550 A | 8/1990 | Wallach et al. | |
| 5,066,335 A | 11/1991 | Lane et al. | |
| 5,147,135 A | 9/1992 | List et al. | |
| 5,147,343 A | 9/1992 | Kellenberger | |
| 5,247,072 A | 9/1993 | Ning et al. | |
| 5,274,048 A | 12/1993 | Engelhardt et al. | |
| 5,340,853 A | 8/1994 | Chmelir et al. | |
| 5,360,903 A | 11/1994 | Lane et al. | |
| 5,367,068 A | 11/1994 | Lane et al. | |
| 5,415,643 A | 5/1995 | Kolb | |
| 5,470,964 A | 11/1995 | Qin | |
| 5,550,189 A | 8/1996 | Qin et al. | |
| 5,823,674 A | 10/1998 | Liechti et al. | |
| 6,039,469 A | 3/2000 | Palmer | |
| 6,063,914 A | 5/2000 | Wolf et al. | |
| 6,387,495 B1 | 5/2002 | Reeves et al. | |
| 6,589,929 B2 | 7/2003 | De Lima et al. | |
| 6,660,211 B2 | 12/2003 | Topolkaraev et al. | |
| 6,734,298 B1 | 5/2004 | Barbucci et al. | |
| 6,765,042 B1 * | 7/2004 | Thornton et al. | ............. 523/400 |
| 8,361,926 B2 * | 1/2013 | Tian et al. | ..................... 502/404 |
| 2004/0157734 A1 | 8/2004 | Mertens | |
| 2005/0288641 A1 | 12/2005 | Soerens | |
| 2013/0040811 A1 * | 2/2013 | Tian et al. | ..................... 502/404 |

FOREIGN PATENT DOCUMENTS

| | | |
|---|---|---|
| DE | 1016248 A | 9/1957 |
| DE | 1567368 A1 | 9/1971 |
| DE | 2543187 A1 | 3/1977 |
| DE | 4013047 A1 | 11/1990 |
| DE | 4033007 A1 | 4/1992 |
| DE | 19654745 A1 | 7/1996 |
| DE | 19533693 A1 | 3/1997 |
| DE | 19536944 A1 | 4/1997 |
| DE | 19729272 A1 | 1/1999 |
| EP | 0339461 B1 | 11/1989 |
| EP | 0538904 A1 | 4/1993 |
| EP | 0601529 B1 | 6/1994 |
| EP | 0699793 A1 | 3/1996 |
| EP | 0855405 A1 | 7/1998 |
| EP | 0900807 A | 3/1999 |
| KR | 10-0197827 B | 6/1999 |
| WO | 9730090 A1 | 8/1997 |
| WO | 9827117 A | 6/1998 |
| WO | 0021581 | 4/2000 |
| WO | 02096953 A1 | 12/2002 |
| WO | 03022887 A1 | 3/2003 |
| WO | 2004085481 A1 | 10/2004 |

OTHER PUBLICATIONS

Felt, Olivia and Burt, Pierre and Gurny, Robert, Drug Development and Industrial Pharmacy, "Chitosan: A Unique Polysaccharide for Drug Delivery", vol. 24 (11), pp. 979-993 (1998).*
W.M. Kulicke, Y.A. Aggour and M.Z. Elsabee, Preparation, Chracterization and Rheological Behavior of Starch-Sodium Trimetaphosphate Hydrogels, Copyright 1990, pp. 134-141, Hamburg-FRG.
International Search Report completed on Nov. 16, 2005 in PCT/EP2005/006619.
Translation of the International Preliminary Report on Patentability mailed on Aug. 30, 2006 in PCT/EP2005/006619.

* cited by examiner

*Primary Examiner* — Wu-Cheng Winston Shen
*Assistant Examiner* — Yih-Horng Shiao
(74) *Attorney, Agent, or Firm* — Smith Moore Leatherwood LLP; Philip P. McCann; John P. Zimmer

(57) ABSTRACT

The present invention relates to a process for producing a water-absorbent polysaccharide including the process steps of bringing into contact an uncrosslinked polysaccharide with a polyphosphate or a polyphosphoric acid as crosslinking agent in the presence of water to form a polysaccharide gel and crosslinking the polysaccharide gel. The invention further relates to a water-absorbent polysaccharide obtainable by this process, a water-absorbent polysaccharide, a composite, a process for producing a composite, a composite produced by this process, the use of the water-absorbent polysaccharides or of the composites as well as the use of polyphosphates.

19 Claims, 7 Drawing Sheets

WATER-ABSORBING POLYSACCHARIDE AND METHOD FOR PRODUCING THE SAME

This application is a national stage application under 35 U.S.C. 371 of international application No. PCT/EP2005/006619 filed Jun. 20, 2005, and claims priority to German Application Nos. DE 10 2004 029 713.4 filed Jun. 21, 2004; DE 10 2004 030 182.4 filed Jun. 22, 2004; and DE 10 2005 013 893.4 filed Mar. 24, 2005; the disclosures of which are expressly incorporated herein by reference.

BACKGROUND OF THE INVENTION

The present invention generally relates to a process for producing a water-absorbent polysaccharide, a water-absorbent polysaccharide obtainable by this process, a water-absorbent polysaccharide, a composite, a process for production of a composite, a composite produced by this process, the use of the water-absorbent polysaccharides or of the composites and the use of polyphosphates.

Most of the absorption materials used today, which are able to absorb in a short time large quantities of liquids (water, urine), are primarily based upon slightly crosslinked synthetic polymers. These include, for example, polymers and co-polymers based upon acrylic acid or acrylamide, which are not based upon renewable materials and are insufficiently or not at all biologically degradable.

In the prior art, however, are described numerous water-absorbing polymers which are based upon polysaccharides and which are at least partially biodegradable. The raw materials for the production of superabsorbers based upon polysaccharides are, however, frequently water-soluble and must be converted into the water-insoluble form, in order to be able to use them as superabsorbers for hygiene applications.

EP 0 538 904 A1 and U.S. Pat. No. 5,247,072 describe superabsorbers based upon carboxyalkylpolysaccharides. In the process, the carboxyalkylpolysaccharide is dissolved in water and isolated by drying or precipitation and then thermally crosslinked via internal ester bridges by the reaction of the hydroxyl groups of the polysaccharide skeleton with the acidic carboxyl groups. Since this crosslinking reaction is very sensitive to small changes of the pH value, the temperature or the reaction duration, absorbers with widely varying absorption properties are obtained. The materials are characterized by a high absorption capacity under pressure, which, however, falls to a fraction of the original absorption properties within a few weeks, upon storage of the absorber.

In U.S. Pat. No. 5,550,189 are described absorbers based upon carboxyalkylpolysaccharides, in which the aging stability is improved by addition of multifunctional crosslinkers, such as, e.g. aluminium salts or citric acid. The production of the absorbers occurs from a common, homogeneous aqueous solution of carboxyalkylpolysaccharide and crosslinker, in which the components are present in low concentration, isolated together and then thermally crosslinked. The synthesis of these absorbers requires a high energy and time consumption, since the aqueous solutions are only of very low concentration. The improvement of the aging stability in the many exemplary embodiments does not correspond to the demands relevant in practice.

EP 855 405 A1 deals with the problem of the lacking aging stability of the absorption capacity of swellable starch maleates and proposes as solution an attachment of mercapto compounds to the double bond of the maleic acid substituents. The absorption behavior of the products, in particular under pressure, is very low.

In U.S. Pat. No. 4,952,550 the production of an absorber based upon carboxymethylcellulose is described, wherein the carboxymethylcellulose in water or organic solvent is treated with multivalent metal salts and a hydrophobizing component. A thermal crosslinking is not carried out. According to the disclosure, the gel blocking in these absorbers is reduced by the hydrophobizing component.

In the processes known from the prior art for crosslinking of polysaccharides, however, besides the partially low aging stability, it is observed that the homogeneous crosslinking of the polysaccharides hinders the biodegradability of the absorber, since the accessibility for microorganisms is reduced by the restricted swelling. Furthermore, in the crosslinking reactions known from the prior art, the enzymatic breakdown is inhibited by the additionally introduced substituents [Mehltretter et al., Journal of the American Oil Chemists Society, 47 (1970), pages 522-524].

In order to improve these disadvantageous properties, it was proposed to limit the crosslinking of the polysaccharide to the surface area, which, however, leads to products which do indeed have a satisfactory absorption under pressure, however, are frequently characterized by only an unsatisfactory absorption capacity under normal pressure and above all, caused by the restriction of the crosslinking to the surface area, by a low gel strength compared to homogeneously crosslinked polymers. Low gel strength leads to the formation of fine dust parts during processing processes, such as, for example, sieving or conveying, and thereby to health impacts of the workers involved in the production of the superabsorbers.

WO 02/096953 A1 describes a process for producing superabsorbers based upon surface-modified polycarboxypolysaccharides, in which an uncrosslinked polysaccharide is swollen with water to form a hydrogel, the hydrogel is then mechanically comminuted and dried and then the thus-obtained polymer particles are coated with a solution of a crosslinker and subjected to a surface crosslinking. Disadvantageous in the process described in WO 02/096953 A1 is, however, that in the formation of the hydrogel an organic solvent must be added to the water, in order to induce the swelling of the polysaccharide. The addition of the organic solvent however leads to the swollen polysaccharide being extremely "slimy", which makes their further processing significantly more difficult. Furthermore, the organic solvents remain at least partially in the end product, which is questionable for ecological reasons. WO 00/21581 A1 also discloses a process in which gels made from crosslinked polysaccharides are brought into contact with organic solvents, in order to obtain absorbent polysaccharides with improved absorption properties. Disadvantageous in this process is the use of organic solvents.

U.S. Pat. No. 5,470,964 describes the production of an absorber based upon acid group-containing polysaccharides at the surface with multivalent metal ions, which has an improved absorption against pressure. Disadvantageous in this process is that for the improved absorption capacity of the absorber against pressure a relatively thick layer of the surface must be crosslinked and that according to the disclosure this is only possible with prior swelling of the polysaccharide with large quantities of solvent. In the swollen state the multivalent metal ions can then penetrate deeply enough into the surface. In order to achieve this, the polysaccharide is added to an excess of the aqueous metal salt solution, wherein the water excess lies in a 2-fold to 40-fold amount based upon the polysaccharide. By means of the thick crosslinked surface layer, good absorption values against pressure are indeed achieved, the free swell capacity as well as the retention capacity of the absorber is, however, disadvantageously reduced. It is further disadvantageous in the described process that the part of the polysaccharide added last to the crosslinker solution in the production process has available less swelling time and a reduced crosslinker concentration, so that an inhomogeneous distribution of the crosslinker results upon the surface, whereby wide variations of the absorption properties arise.

In general, one aspect of the present invention is to overcome the disadvantages arising from the state of the art. In particular, one aspect of the present invention provides biodegradable, superabsorbent polymers based upon renewable raw materials, which do not have the above described deficiencies. In particular, the absorber should have a high long-term storage stability, in which the absorption properties remain as far as possible. At the same time it is intended that the absorber particles have a high mechanical stability, in order to avoid the formation of fine dust parts during processing processes such as, for example, sieving or conveying.

Furthermore, regarding the absorption behavior, the absorbers should not tend to gel blocking, in particular in absorption layers comprising a lot of superabsorber (mostly more than about 65 wt % based upon the absorbent layer) and besides a high absorption and retention capacity also possess a high absorption capacity against pressure for water and aqueous solutions.

In absorbent layers or cores comprising a lot of superabsorber, and diapers comprising these, a wetting through characterized as leakage is often observed. This, and the gel blocking, are usually due to a slimy swollen hydrogel or at least to slimy components of the hydrogel. An object of this invention is thus to make available a less slimy hydrogel-forming absorbent polymer, which is suitable for use in hygiene articles. For a good absorption and application behavior it is necessary that the absorber has a predominantly insoluble character also in an excess of aqueous solution. Furthermore, the absorbers should be characterized by a particularly good biodegradability and be as free as possible from organic solvents.

A further aspect of the invention finds a production process for such superabsorbent polymers, which is simple, economical and can be reliably carried out, delivers a uniform product quality and in which small quantities of solvents are used and organic solvents are avoided if possible. Furthermore, it should be possible to carry out the process without the use of toxicologically questionable substances.

In addition, an aspect of the present invention consists in improving the biodegradability of hygiene articles such as sanitary napkins, wound dressings, incontinence articles and diapers.

DRAWINGS

The foregoing and other features, aspects and advantages of the present invention will become better understood with regard to the following description, appended claims and accompanying drawings where:

DESCRIPTION OF THE PRESENT INVENTION

Figure 1:
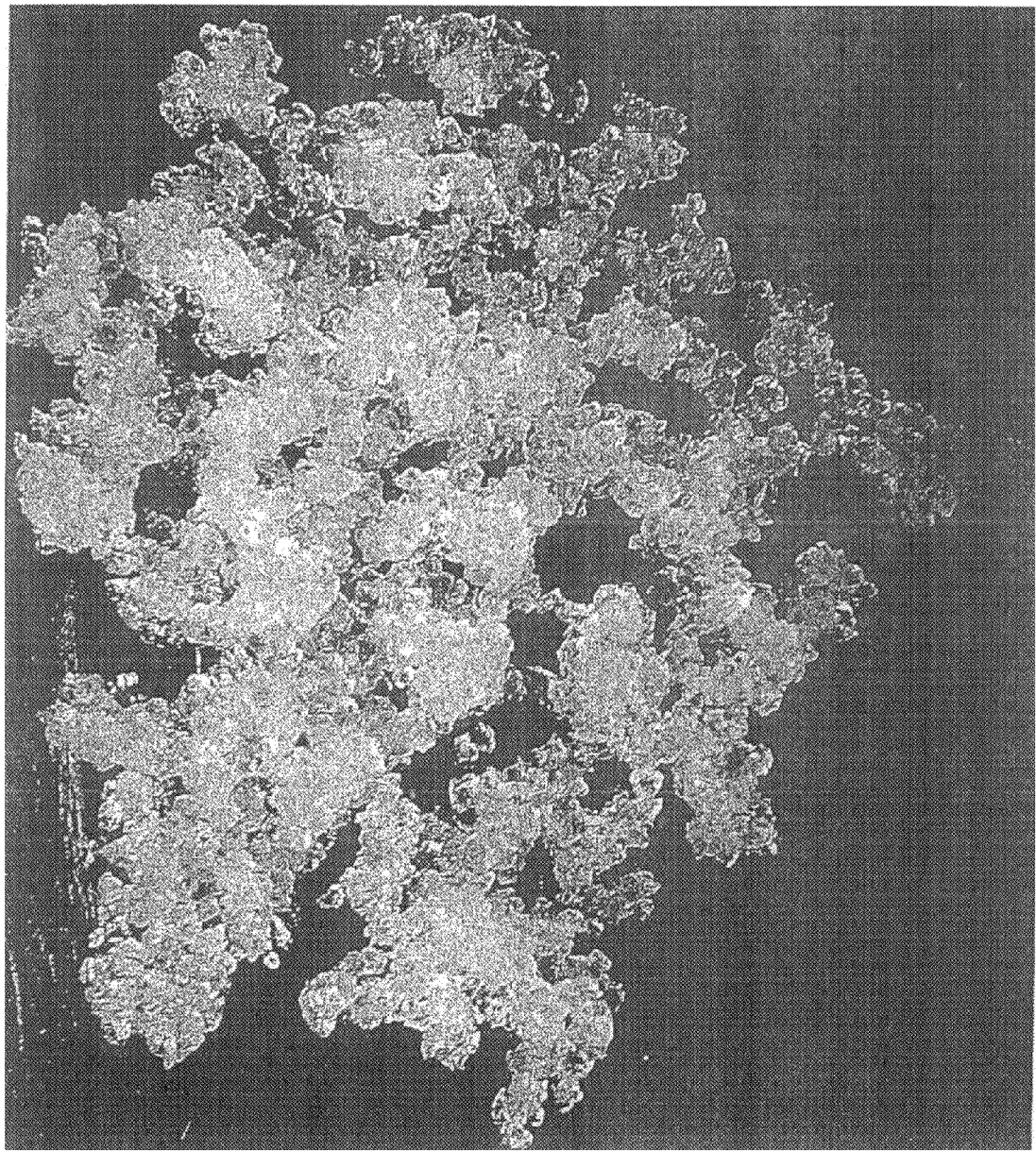
FIG. 1 is a picture of individual gel particles that do not stick together.

The foregoing aspects of the invention are achieved by a process for producing a water-absorbing polysaccharide comprising the process steps of: bringing into contact an uncrosslinked polysaccharide with a polyphosphate or with polyphosphoric acid as crosslinking agent in the presence of water to form a polysaccharide gel, whereby the polysaccharide swells; and crosslinking the polysaccharide gel.

A further aspect of the present invention is formed by a process for producing a water-absorbing polysaccharide comprising the process steps of bringing into contact a polysaccharide with a crosslinking agent in the present of water to form a polysaccharide gel, and drying the polysaccharide gel, whereby at least the bringing into contact occurs in a kneader. In one aspect of the invention, in the kneader a homogeneous and intimate mixing of the crosslinking agent with the polysaccharide as possible occurs. The crosslinking may primarily occur in the drying step. Also in this embodiment of the process according to the invention, the crosslinking agent may be a polyphosphate or polyphosphoric acid.

In a further aspect of the invention, the kneader has at least two kneading shafts. The at least two kneading shafts may have a contour which at least partially reaches into each other. There may be elements attached to the kneading shaft such as disks, paddles, anchors, or hooks, which form rotation radii seen from the central axis of the kneading shaft, which overlap with the rotation radii of the element arranged at a further kneading shaft. This can, for example, be achieved by arranging the kneading shafts at least in sections axially parallel to each other, and selecting the distance of the central axis of the kneading shaft at the axially parallel section to be so small that the elements formed on the kneading shaft at least partially overlap during operation of the kneading shaft. In another aspect of the process according to the invention, at least one part of the elements formed on the kneading shaft are arranged and designed in such a way that these convey the goods to be conveyed at least partially parallel to the central axis of the kneading shaft, wherein the at least two kneading shafts form a conveying channel which runs at least partially axially at least to one of the kneading shafts. In this way, on the one hand, a homogeneous mixing of the polysaccharide with the crosslinking agent as possible can be achieved, and the homogeneous mixture comprising the polysaccharide and the crosslinking agent can be continued to the crosslinking, or drying step which occurs by means of temperature treatment.

In connection with the homogenization, in one aspect of the invention, the portion of already reacted crosslinking agent is not greater than about 30 wt %, such as not greater than about 20 wt %, such as not greater than about 10 wt %, and such as not greater than about 5 wt %, respectively based upon the crosslinking agent. The portion of already reacted crosslinking agent can be determined by subtraction of the determinable free crosslinking agent from the originally used amount.

In an embodiment of the process according to the invention, the mixing of the polysaccharide and crosslinking agent takes place in a kneader, whereas the crosslinking or drying step following from the mixing occurs in a device being different from the kneader, such as in a belt drier. A comminution step, such as a chopping or milling step can be provided between the two steps, in order to increase the surface area of the product to be dried or crosslinked.

In one aspect of the invention, between the temperatures of the mixing for homogenization and of the drying, or crosslinking there is a temperature difference. The two temperatures differ by at least about 10° C., such as by at least about 20° C., such as by at least about 40° C., and such as by at least about 80° C. In an embodiment of the process according to the invention, the temperature during the mixing for homogenization lies within the range from about 2° C. to about 40° C., such as within the range from about 10° C. to about 35° C., and such as within the range from about 15° C. to about 30° C. To adjust these suitable temperatures, the temperature of the kneader may be controlled. Either the housing surrounding the kneading shaft(s) or the kneading shafts, optionally with the thereupon arranged elements themselves, or both, can be temperature-controlled.

In the process according to the invention, using the kneader, a kneader energy within the range from about 0.01 to about 1 MJ/kg, such as within the range from about 0.25 to about 0.75 MJ/kg and such as within the range from about 0.3 to about 0.7 MJ/kg as well as a specific torque of about 0.1 to about 70 Nm/l, such as within the range from about 5 to about 50 Nm/l and such as within the range from about 10 to about 40 MJ/kg can be applied. Suitable kneaders are among others described in DE 195 36 944 A1, U.S. Pat. No. 5,147,135 and DE 195 33 693 A1. In addition, suitable kneaders can be obtained commercially, for example from List AG, Arisdorf, Switzerland.

In the process according to the invention, the polysaccharide may be a non-crosslinked polysaccharide. The crosslinking agent can be any suitable crosslinking agent, such as polyphosphate, or polyphosphoric acid, or a mixture of at least two thereof. In a further aspect of the invention, the polyphosphate or polyphosphoric acid may be combined with other suitable further crosslinking agents. Suitable further crosslinking agents are, for example, aluminium chloride or citric acid, as described in WO 02/096953 A1, or polyamines, as described in U.S. Pat. No. 6,734,298.

By the use of polyphosphates or polyphosphoric acids as crosslinking agent for polysaccharides according to the process according to the invention, water-absorbent polysaccharides are obtainable which distinguish themselves through an excellent absorption and retention capacity for water, aqueous solutions, and body fluids. Furthermore, the water-absorbent polysaccharide obtainable by the process according to the invention is storage-stable, substantially free from residual monomers, and organic solvents, and only soluble in aqueous liquids to a very small degree, and to a large degree biodegradable.

The polysaccharides used in the process according to the invention are water-soluble, or water-swellable, and are used in non-crosslinked form. They can be modified with further groups besides the hydroxyl groups, in particular with such groups that improve the water solubility. To such groups belong, for example, the carboxyl group, the carboxylalkyl group, such as the carboxymethyl group, the hydroxyalkyl group, in particular the hydroxymethyl group, and/or the hydroxyethyl group, such as the hydroxymethyl group, as well as the phosphate group.

Depending upon the functional modification, the polysaccharides used in the process according to the invention can be based upon electrically charged, or upon electrically uncharged polysaccharides. A use of a polysaccharide mixture based upon electrically charged and electrically uncharged polysaccharide is also conceivable. Starches or starch derivatives, such as, hydroxypropyl starches, amylose, amylopectin, cellulose or cellulose derivatives, for example, ethyl hydroxyethylcellulose, or hydroxylpropylcellulose, or polygalactomannanes such as guar or carob seed flour belong to the electrically uncharged polysaccharides according to the invention.

To the electrically charged polysaccharides according to the invention belong in particular polycarboxypolysaccharides. The polycarboxypolysaccharides used in the process according to the invention may be derived either from polysaccharides which do not naturally comprise any carboxyl groups, and are provided with carboxyl groups by subsequent modification, or they already comprise naturally carboxyl groups, and are optionally subsequently provided with further carboxyl groups by modification. To the first group of polysaccharides belong, for example, oxidized starches, carboxylated phosphate starches, oxidized cellulose, carboxymethylcellulose, or carboxymethyl starches, such as carboxymethylcellulose (CMC). To the polysaccharides, which already comprise naturally carboxyl groups, belong, for example, xanthane, alginate, or gum Arabic.

According to the invention, polycarboxypolysaccharides such as, for example, carboxymethyl guar, carboxylated hydroxyethyl, or hydroxypropyl cellulose, carboxymethyl cellulose and carboxymethyl starches, oxidized starches, xanthane and mixtures of the individual polycarboxypolysaccharides are used as polysaccharide, such as carboxymethyl cellulose. In principle, polycarboxypolysacccharide derivatives with low and high degrees of carboxyl substitution can be used in the process according to the invention. They may have an average degree of carboxyl substitution within the range from about 0.3 to about 1.5, such as polycarboxypolysaccharide derivatives with a degree of substitution within the range from about 0.4 to about 1.2.

In one embodiment of the process according to the invention, the polycarboxypolysaccharides are used with an addition of carboxyl groups-free polysaccharides. Strongly swelling polysaccharides, such as, for example, polygalactomanine or hydroxyalkyl celluloses may be employed. The quantities of carboxyl groups-free polysaccharides to be used for modification are determined by the required property profile, such as about 20 wt %, such as about 10 wt %, and such as about 5 wt % are used, based upon the uncrosslinked polycarboxypolysaccharide.

The carboxyl groups-free polysaccharides can be mixed with the uncrosslinked polycarboxypolysaccharide before the bringing into contact with the polyphosphate or the polyphosphoric acid or mixed with the polycarboxypolysaccharide after the bringing into contact of the uncrosslinked polycarboxypolysaccharide with the polyphosphate or the polyphosphoric acid. It is also conceivable that the carboxyl groups-free polysaccharides are initially brought into contact with the polyphosphate or the polyphosphoric acid or with an aqueous solution comprising the polyphosphate or the polyphosphoric acid and the thus-obtained mixture is then mixed with the polycarboxypolysaccharide.

The carboxyl groups of the uncrosslinked polycarboxypolysaccharides used in the process according to the invention may be neutralized to at least about 50 mol %, such as to at least about 80 mol %, such as to at least about 90% and such as to about 100 mol %. As neutralization agents, alkali hydroxides such as sodium and potassium hydroxide, sodium and potassium carbonates or hydrocarbonates and ammonium hydroxide and amines have proved themselves.

The water-soluble polysaccharides used in the process according to the invention may have a high average molecular weight in the scope of the molecular weight distribution given by the natural polymer construction and thereby also a high solution viscosity in dilute aqueous solution such as, e.g. carboxymethylcellulose prepared from cotton lint. Polysaccharides with a solution viscosity in one percent aqueous solution of more than 2,000 mPas may be utilized. If a polycarboxypolysaccharide is used in the process according to the invention, this should have a solution viscosity in one percent aqueous solution of more than about 5,000 mPas, and such as more than about 7,000 mPas.

Because of the production process, polysaccharides can comprise varyingly high salt amounts as side components. Typical salt contents of carboxymethylcelluloses utilized as polysaccharides according to the invention lie at around about 0.5 wt % for food qualities, within the range from around 2 wt % in technical qualities up to about 25 to about 50 wt % for products in applications as protective colloids. Although the water-absorbing polysaccharides obtained by the process according to the invention have a high tolerance with respect to salt load, the uncrosslinked polysaccharides to be used should have a salt quantity of not more than about 20 wt %, such as not more than about 15 wt %, such as not more than about 5 wt % and such as not more than about 2 wt % salt, respectively based upon the weight of the uncrosslinked polysaccharide used in the process according to the invention.

The physical form of the polysaccharides used in the process according to the invention is unimportant for the properties of the water-absorbing polysaccharides obtainable by the process according to the invention. Thus the polysaccharides can be used, e.g. in the form of powders, fine powders, granulates, fibres, flakes, beads, or compacts, wherein the use of powdery materials with a particle size within the range of about 1 to about 2,000 μm may be used because of the simple dosability, and conveyability.

As polyphosphate or polyphosphoric acid, chain polyphosphates (catena-phosphates), or ring polyphosphates (cyclophosphates, also described as "metaphosphates") may be used, wherein the polyphosphates are the salts and the esters of polyphosphoric acids. In one aspect of the invention, polyphosphates are compounds of the composition $M_{n+2}^{I}[P_nO_{3n+1}]$ or $M_n^{I}[H_2P_nO_{3n+1}]$, such as compounds of the structure $M_n^{I}[H_2P_nO_{3n+1}]$. Among these, compounds of the composition $Na_nH_2P_nO_{3n+1}$ may be used, such as for example the "Grahamsche salt", the "Maddrellsche salt", the "Kurrolsche salt" or "Calgon" used in washing agents. In another aspect of the invention, metaphosphates are compounds of the composition $M_n^{I}[PO_3]_n$. In the above cited formula, $M^I$ stands for monovalent metal, such as for sodium or potassium. n may have a value of at least 2, such as at least about 10 and such as at least about 50, wherein a value of about 5,000, such as of about 1,000, and such as of about 100 is not exceeded.

In an embodiment of the process according to the invention polyphosphates are used which have been prepared by condensation of dihydrogen monophosphates and in which the H atoms of the acidic groups bound as chain groups are not replaced by metal. The polyphosphates may have a composition $M_n^{I}[H_2P_nO_{3n+1}]$, wherein $M^I$ and n have the above detailed meaning. Polyphosphoric acids may be obtained by the controlled addition of water to $P_4O_{10}$ or by condensation during heating of $H_3PO_4$. The polyphosphoric acids according to the invention may have the composition $H_{n+2}P_nO_{3n+1}$ or $(HPO_3)_n$, whereby polyphosphoric acids of the composition $(HPO_3)_n$ are also described as metaphosphoric acids, whereby n has a value of at least about 2, such as at least about 10, such as at least about 20, and such as at least about 50, wherein a value of about 10,000, such as of about 1,000, and such as of about 100 is not exceeded. With increasing value of n, the above-mentioned composition of $H_{n+2}P_nO_{3n+1}$ approaches the composition $(HPO_3)_n$ of the metaphosphoric acids.

According to an aspect of the invention, a polyphosphate or polyphosphoric acid is brought into contact, or mixed, with the uncrosslinked polysaccharide, in a quantity within a range from about 0.001 to about 20 wt %, such as in a quantity within a range from about 0.01 to about 10 wt % and such as in a quantity within a range from about 0.05 to about 5 wt %, respectively based upon the weight of the uncrosslinked polysaccharide. According to another aspect of the invention, the polyphosphate or the polyphosphoric acid is brought into contact with the uncrosslinked polysaccharide in the presence of water at a temperature within a range from about 15 to about 60° C., such as within a range from about 18 to about 40° C. and such as within a range from about 20 to about 30° C. In a further aspect of the invention, the bringing into contact of the polyphosphate or the polyphosphoric acid with the polysaccharide occurs at room temperature.

The above mentioned polyphosphates or polyphosphoric acids can be used alone or also in combination with other crosslinkers which are not based upon polyphosphates or polyphosphoric acids, for crosslinking of the polysaccharide. As additional crosslinkers, which are not, based upon polyphosphates or polyphosphoric acids those crosslinkers, which are cited in WO 02/096953 A1 as covalent ionic or post crosslinking agents, as well as those crosslinkers which are cited in WO 00/21581 A1 on page 6 in the first paragraph may be utilized. In one aspect, the weight proportions between these other crosslinkers which are not based upon polyphosphate or polyphosphoric acids and the polyphosphates or polyphosphoric acids lies within a range from about 1:0.01 to about 1:50, such as within a range from about 1:0.1 to about 1:20, and such as within a range from about 1:1 to about 1:10.

The swelling time is dependent upon the temperature at which the polyphosphate or the polyphosphoric acid is brought into contact with the uncrosslinked polysaccharide as well as from the starting compounds employed and can be easily determined by simple pre-experiments. In one aspect of the invention, the first process step of the process according to the invention is then finished when no further volume increase of the polysaccharides as a result of the swelling can be observed. In another aspect, the bringing into contact of the polyphosphate or the polyphosphoric acid with the uncrosslinked polysaccharide occurs for a time period of about 1 minute to about 48 hours, such as from about 1 hour to about 24 hours, and such as from about 12 to about 20 hours.

In one aspect of the invention, the bringing into contact with the uncrosslinked polysaccharide with the polyphosphate or with the polyphosphoric acid occurs at a pH value within a range of about 7 to about 13, such as within a range from about 7.5 to about 12.5 and such as within a range from about 8 to about 12. This is particularly the case if a polycarboxypolysaccharide is used as polysaccharide. By adjusting the pH value within the above given pH ranges, an at least partial neutralization of the carboxyl groups present in the polysaccharide occurs. In addition, the polyphosphoric acid is likewise at least partially neutralized.

In an embodiment of the process according to the invention, the mixing of the uncrosslinked polysaccharide with the polyphosphate or the polyphosphoric acid occurs in such a way that initially the polyphosphate, or the polyphosphoric acid, is dissolved or dispersed in water, in the aqueous solution or the aqueous dispersion of the polyphosphate or the polyphosphoric acid, a pH value is adjusted within a range from about 7 to about 13, such as from about 7.5 to about 12.5, and such as from about 8 to about 12, and then the aqueous solution or the aqueous dispersion of the polyphosphate or the polyphosphoric acid is mixed with an uncrosslinked polysaccharide.

In another embodiment of the process according to the invention the mixing of the uncrosslinked polysaccharide with the polyphosphate or the polyphosphoric acid occurs in such a way that the uncrosslinked polysaccharide is initially mixed with the polyphosphate or the polyphosphoric acid under dry conditions, and the thus-obtained mixture is then brought into contact with water. In this way, by addition of acids or bases to the water or to the mixture of the polycarboxypolysaccharide and the polyphosphate or the polyphosphoric acid it is assured that the bringing into contact of the uncrosslinked polysaccharide with the polyphosphate or the polyphosphoric acid occurs at a pH value within a range from about 7 to about 13, such as from about 7.5 to about 12.5, and such as from about 8 to about 12.

In a further embodiment of the process according to the invention the mixing of the uncrosslinked polysaccharide with the polyphosphate or the polyphosphoric acid occurs in such a way that initially the uncrosslinked polysaccharide is brought into contact with water and then the swollen polysaccharide is brought into contact with the polyphosphate or the polyphosphoric acid. It is also thus assured that, by addition of acids or bases to the water or to the polysaccharide which has been brought into contact with the water or to the polyphosphate or the polyphosphoric acid respectively, that the bringing into contact with the uncrosslinked polysaccharide with the polyphosphate or the polyphosphoric acid occurs at a pH value within a range from about 7 to about 13, such as from about 7.5 to about 12.5, and such as from about 8 to about 12.

In a further aspect of the present invention, the mixing of the uncrosslinked polysaccharide with the polyphosphate or the polyphosphoric acid occurs in the presence of an additive, whereby the additive can be previously combined with the uncrosslinked polysaccharide or with the polyphosphate or the polyphosphoric acid or added to the uncrosslinked polysaccharide which has already been brought into contact with the polyphosphate or the polyphosphoric acid. If the bringing into contact of the uncrosslinked polysaccharide with the polyphosphate or the polyphosphoric acid occurs in such a way that initially an aqueous solution or an aqueous dispersion of the polyphosphate or the polyphosphoric acid is prepared, which is then added to the polysaccharide, then the additive can also be added to the aqueous solution or the aqueous dispersion of the polyphosphate or the polyphosphoric acid.

The additives can be added in a quantity within a range from about 0.01 to about 20 wt %, such as in a quantity within a range from about 0.1 to about 10 wt %, and such as in an amount within a range from about 1 to about 5 wt %, respectively based upon the weight of the uncrosslinked polysaccharide. In one aspect, the additives are anti blocking additives, which improve the processability of the hydrogel produced and which remain at least partially in the product after drying. In another aspect, anti blocking additives are native or synthetic fibre materials or other materials with a large surface area, e.g. from the group of silica gels and synthetic silicic acids and water-insoluble mineral salts.

Further exemplary additives are water-soluble additives from the group of bases salts and blowing agents. As blowing agents are selected inorganic or organic compounds that liberate gas under the influence of catalysts or heat, for example azo and diazo compounds, carbonate salts, ammonium salts or urea. Further additives are pH regulators such as e.g. alkali metal hydroxides, ammonia, basic salts such as e.g. alkali metal carbonates or acetates. Further additives are neutral salts, such as, e.g. alkali metal or alkaline earth metal sulfates or chlorides for regulation of the ionic strength of the solution or of the salt content of the powdery absorber resin. Furthermore, water-miscible organic solvents, for example boiling less than 100° C. can be used as additive in the aqueous hydrogel. During the following drying these volatile organic solvents substantially escape from the hydrogel. These solvents are then finally volatilised during the subsequent surface post-crosslinking.

The bringing into contact, or mixing, of the uncrosslinked polysaccharide with the polyphosphate or the polyphosphoric acid in the presence of water can occur continuously or discontinuously, such as continuously. Suitable mixing devices are e.g. discontinuous kneaders such as VAT kneaders, interior mixers or continuous kneaders such as one-, two- or multishaft mixers.

During the production of the polysaccharide gel in the first process step of the process according to the invention, the polysaccharide content in the mixture of polysaccharide, water and polyphosphate or polyphosphoric acid can vary within wide limits, in one embodiment of the process it lies within the range from about 5 to about 65 wt %, such as about 10 to about 50 wt %, and such as from about 15 to about 30 wt %.

In one embodiment of the invention, respectively the water, the aqueous solution or aqueous dispersion of the polyphosphate or the polyphosphoric acid is continuously added to the dry raw material polysaccharide, for example in an extruder, whereby the process is carried out in such a way that the water is present as minority component. The mixture of polysaccharide, polyphosphate or polyphosphoric acid and water can additionally comprise according to the invention up to about 30 wt %, such as up to about 20 wt % of one or more organic solvents which are miscible with water and immiscible with the polysaccharide. However, in one aspect of the invention, the bringing into contact with the uncrosslinked polysaccharide with the polyphosphate or with the polyphosphoric acid occurs in the absence of an organic solvent.

In another aspect of the invention, the swollen gel is comminuted before the crosslinking. Through the gel comminution, above all the ratio of gel surface to gel volume is increased, whereby the following drying step requires substantially less energy input. The process of gel comminution does not underlie any restriction. In one embodiment, the gel comminution occurs by pressing the gel through a breaker plate into gel strands, which can optionally be fragmented into shorter gel strands by a cutting apparatus. The gel consistency can be purposely adjusted via the type and the amount of the addition of polyphosphates or polyphosphoric acids. A use of organic solvents in this regard, as described in WO 02/096953 A1, is here not necessary.

In the second step of the process according to the invention the polysaccharide gel or the comminuted polysaccharide gel is crosslinked to form a crosslinked polysaccharide and in one aspect is dried at the same time to a low residual water content. It is also conceivable to first crosslink the polysaccharide gel under conditions that do not lead to a drying of the polysaccharide gel and only then to dry the crosslinked polysaccharide gel. The crosslinking step can follow directly from the pre-swelling, but it is also possible to store the polysaccharide gels or the comminuted polysaccharide gels respectively before further processing, for a longer period of time, e.g. several weeks, without the properties of the therefrom-resulting superabsorber according to the invention changing.

In one aspect of the invention, the polysaccharide gel is crosslinked and thereby dried at the same time at a temperature of about 70° C., such as above about 100° C., and such as above about 115° C., whereby a crosslinking or drying temperature respectively of about 300° C., such as about 250° C., and such as about 200° C. is not exceeded. It is also conceivable to first dry the polysaccharide gel at lower temperatures than about 70° C., such as under reduced pressure, and only then to heat by increasing the dried polysaccharide to a temperature which enables a crosslinking of the polysaccharide. In principle, the crosslinking step can be carried out at any conceivable temperature, as long as the temperature is high enough to enable an at least partial crosslinking of the polysaccharide gel by the polyphosphate or the polyphosphoric acid and does not exceed a temperature that leads to degradation of the polysaccharide.

Attention should be paid with the crosslinking or drying temperatures respectively that the parameters such as the polymer content of the gel, the pH value of the mixture, the mixing process, the crosslinking or drying temperature respectively and the duration of drying influence each other and may be selected in conjunction with each other in such a way that during the crosslinking of the polysaccharide with the polyphosphate or the polyphosphoric acid no internal crosslinking of the hydrogel occurs. If, e.g. in the production of the polysaccharide gel an aqueous solution with a pH value below about 7 is used, when using polycarboxypolysaccharides a part of the carboxylate groups present in the polysaccharide derivative is converted into the free acid form, which above all towards the end of the drying can function as internal crosslinkers by means of an esterification with the hydroxyl groups. In order to avoid or as far as possible suppress this, in principle undesired, internal crosslinking, the crosslinking or drying respectively in these cases may occur at temperatures within the range from about 70 to about 100° C. The pH value is usually adjusted to about 6 or more. In one embodiment of the invention, for the production of the polysaccharide gel an aqueous solution is selected with a pH value of about 7 or more and the crosslinking or drying respectively carried out at temperatures above about 110° C., such as above about 115 to about 120° C.

Various processes are known for the drying of the polysaccharide gels. Possible processes are, e.g. vapor drying, evaporation drying, radiation drying (example: infrared drying), high frequency drying (example: microwave drying), vacuum drying, freeze drying or spray drying. The drying can thus occur for example according to the thin film drying process, e.g. with the aid of a two axis roll dryer according to the plate drying process, according to which the hydrogel polymer particles are loaded onto plates in several layers in a drying chamber, in which hot air circulates, according to the rotating drum process using roll dryers or according to the conveyor belt process, in the following also described as belt drying. Belt drying, in which trays provided with holes of a circular conveyor in a tunnel is charged with product to be dried and product is dried during the conveying by the blowing of hot air through the tray holes, represents the most economical drying process for water-swellable hydrophilic hydrogels.

In one aspect of the invention, the moisture of the polymer obtained by drying the polysaccharide gel does not lie above about 30 wt %, such as not above about 15 wt %, and such as not above about 10 wt %. If the polysaccharide gel is produced in a continuous mixer, for example in an extruder, the initial products which are not yet post-crosslinked at the surface can, at pH values of about 7 and above, have high retentions of greater than or equal to about 40 g/g, which prove to be stable upon tempering above about 60 minutes and about 120° C. and only differ slightly from products which have been prepared with higher pH values. If the hydrogels are prepared, on the other hand, in a batch process, the stability with respect to a tempering increases with increasing pH value of the gel. An exemplary pH setting for the formation of hydrogel in the batch process therefore lies at pH about 10 or more.

In a further embodiment of the process according to the invention, in an additional process step the crosslinked polycarboxypolysaccharide obtained after the drying of the polysaccharide gel or respectively the comminuted polysaccharide gel is milled in a further process step. Through the comminution of the polysaccharide gel as well as by the milling of the dried, crosslinked polycarboxypolysaccharide, particulate, crosslinked polysaccharides are obtained. For the subsequent milling of the dried polysaccharide gels or respectively the dried and previously comminuted polysaccharide gels the product may be cooled to be dried in the last section of the belt drying to temperatures less than about 70° C., such as about 60° C., and such as less than about 50° C. The dried, cooled polysaccharide gels or respectively comminuted polysaccharide gels are first pre-broken, for example using a finger breaker. The thus pre-comminuted dried gel particles are then milled, whereby in one aspect of the invention the milling occurs using a roller mill, in order to maintain the production of fine particles as small as possible. In one embodiment, the milling occurs in two steps, first via a cause roller mill, then via a fine roller mill, whereby the latter can in turn be in one or two steps.

By means of the subsequent sieving, the particle size distribution is adjusted, which generally lies between about 10 and about 3000 µm, such as between about 100 and about 2000 µm, and such as between about 150 and about 850 µm. Particles which are too course can be subjected to the milling again, particles which are too fine can be recycled in the production process.

In one embodiment of the process according to the invention a further process step follows the drying step or the milling step respectively, in which the particulate, crosslinked polysaccharide is post-crosslinked in the outer part of the particle with a post-crosslinking agent. As outer part of the particle is understood each volume element of the particle whose distance to the center of the particle may be at least about 75%, such as at least about 85%, and such as at least about 95% of the outer radius of the polymer particle.

In one aspect of the invention, the surface crosslinking of the dried, particulate, crosslinked polycarboxypolysaccharide occurs with about 0.001 to about 25 wt %, such as with about 0.1 to about 20 wt % of the post-crosslinking agent, respectively based upon the weight of the crosslinked polysaccharide. The post-crosslinking agent may be used in the form of an about 0.01 to about 80 wt %, such as an about 0.1 to about 60 wt % solution. The addition of the post-crosslinking agent occurs in suitable mixing aggregates. These are, for example, Patterson-Kelly-mixer, Drais turbulence mixer, Lödige mixer, Ruberg mixer, worm mixer, plate mixer, fluidised bed mixer or Schugi mixer. After spraying on the solution of the post-crosslinking agent, a temperature treatment step can follow, such as in a downstream drier, at a temperature between about 40 and about 250° C., such as about 60 to about 200° C., and such as about 80 to about 160° C. over a time period of about 5 minutes to about 6 hours, such as about 10 minutes to about two hours, and such as about 10 minutes to about 1 hour, whereby solvent parts are removed. The optimal duration of the post-heating can be easily determined for individual crosslinker types with a small number of experiments. It is limited by the fact that the desired property profile of the superabsorber may be destroyed again as a result of heat damage. The thermal treatment can be carried out in conventional driers or ovens, for example rotary kiln ovens, fluidised bed driers, plate driers, paddle driers or infrared driers.

In one embodiment, the aqueous solution of the surface post-crosslinker is adjusted before its use to a temperature of about 15° C. to about 100° C., such as about 20° C. to about 60° C. The covalent surface post-crosslinking can optionally be accelerated by catalysts. Compounds that catalyze the esterification reaction between a carboxyl group and a hydroxyl group, such as, for example, hypophosphite, acetyl acetonate mineral acids may be used as catalysts, such as e.g. sulphuric acid and Lewis acids. In one aspect, sulphuric acid and hypophosphite are used. The weight ratio of surface post-crosslinker to crosslinking catalyst is about 1:0.001 to about 1:1, such as about 1:0.1 to about 2:1. In one embodiment the crosslinking catalysts are mixed with the solution of the surface post-crosslinker.

A post-crosslinking solution can optionally comprise up to about 70 wt. % of one or more additives. Additives are, above all, water-soluble compounds, which lead to the homogeneous distribution of the crosslinker solution on the surface of the absorber, in that they slow down the penetration of the solvent into the interior of the superabsorber particle as well as reducing the solubility of the particle surface and thereby the tendency of the moist superabsorber particles to stick together. Exemplary additives are, besides water-miscible organic solvents such as, for example, ethanol, propanol, 2-propanol, acetone, glycerine, tetrahydrofuran and dioxane, also water-soluble hydrophilic organic solids, in particular polymers such as, e.g. polyalkylene glycols, polyvinyl alcohols, such as polyethylene glycols. The post-crosslinking of the outer part can be carried out by ionic or covalent post-crosslinking agents, which react with the functional molecular groups near to the surface, for example, carboxyl, carboxylate or hydroxyl groups, such as by heating.

As covalent post-crosslinking agents, which can also be used in combination with ionic crosslinkers, such crosslinkers are used, which react with functional groups of the polysaccharides to form covalent bonds. In one embodiment, crosslinkers are used which can react with the hydroxyl groups, or if using polycarboxypolysaccharides, with the carboxyl groups of the crosslinked polysaccharide, for example substances comprising acid groups. In particular, low molecular polycarboxylic acids and derivatives thereof, such as, e.g. malonic acid, maleic acid, maleic acid anhydride, tartaric acid and polymeric polycarboxylic acids, e.g. based upon (meth)acrylic acid and/or maleic acid are suitable. Examples are citric acid, butane tetracarboxylic acid and polyacrylic acid, such as citric acid. The polycarboxylic acids can also be used in partially neutralized form, e.g. by partial neutralization with alkali hydroxides or amine bases. Besides these post-crosslinking agents, in particular also polyphosphates and polyphosphoric acids may be used as post-crosslinking agents, whereby those polyphosphates and polyphosphoric acids may be used which have already been cited in the context of the first process step of the process according to the invention.

Suitable ionic post-crosslinking agents which can be used alone or in combination with the covalent post-crosslinking agents are salts of at least divalent metal cations, for example alkaline earth ions such as $Mg^{2+}$, $Ca^{2+}$, as well as $Al^{3+}$, $Ti^{4+}$, $Fe^{2+}/Fe^{3+}$, $Zn^{2+}$ or $Zr^{4+}$, whereby $Al^{3+}$, $Ti^{4+}$ and $Zr^{4+}$ may be used such as $Al^{3+}$. Aluminium salts may be used in a quantity of about 0.2 to about 1.0 wt. %, such as about 0.25 to about 0.85 wt. %, based upon the crosslinked polysaccharide. The salts of the metal cations can be used alone or mixed with each other. The metal cations in the form of their salts have a sufficient solubility in the solvent used, and in one aspect the metal salts are used with weakly complexing anions such as, e.g. chloride, nitrate, sulphate and acetate. Further suitable post-crosslinking agents are such ones that can form both covalent and ionic crosslinking bonds, e.g. di- and polyamines which can function as both covalent crosslinkers via amide groups, and as ionic crosslinkers via ammonium salt complexes.

In one embodiment of the process according to the invention, polyphosphates or polyphosphoric acids are used as post-crosslinking agent, in another embodiment, a mixture of polyphosphates or polyphosphoric acids and at least one further of the above-mentioned post-crosslinking agents, which is not based upon polyphosphates or polyphosphoric acids, in particular mixtures of polyphosphates or polyphosphoric acids and ionic post-crosslinking agents are used, such as mixtures of polyphosphates or polyphosphoric acids and aluminium salts.

In the use of polyphosphates or polyphosphoric acids as post-crosslinking agent, these may be used in the form of an aqueous solution with a pH value within a range from about 7 to about 13, such as within a range from about 8 to about 12. In the use of polyphosphates or polyphosphoric acids as post-crosslinking agent, it is further exemplary that the polyphosphates or the polyphosphoric acids are used in a quantity within a range from about 0.01 to about 10 wt %, such as in a quantity within a range from about 0.1 to about 5 wt %, and such as in a quantity within a range from about 0.3 to about 1.5 wt %, respectively based upon the weight of the crosslinked polysaccharides. In connection with the post-crosslinking of the crosslinked polysaccharides, in one embodiment of the process according to the invention, the crosslinked polysaccharide is brought into contact with an inorganic material.

An inorganic material, any inorganic material, such as particulate, known to the skilled person, can be brought into contact with the crosslinked polysaccharides, which is suitable for modifying the properties of water-absorbent polymers. To the exemplary inorganic materials belong silicates, in particular scaffold silicates such as zeolites or silicates which have been obtained by drying aqueous silicic acid solutions or silica sols, for example the commercially obtainable products such as precipitated silicic acids and pyrogenic silicic acids, for example aerosils, aluminates, titanium dioxides, zinc oxides, clay materials and further minerals familiar to the skilled person as well as carbon-containing inorganic materials. Exemplary silicates are all natural or synthetic silicates disclosed in "Holleman and Wiberg, Lehrbuch der Anorganischen Chemie, Walter de Gruyter Verlag, $91^{st}$ to $100^{th}$ edition, 1985" on sides 750 to 783, as silicates.

Exemplary silicates are the zeolites. As zeolites, all synthetic or natural zeolites known to the skilled person can be used. Exemplary natural zeolites are zeolites from the natrolite groups, the harmotone groups, the modenite groups, the chabasite groups, the faujasite groups (sodalite groups,) or the analcite groups. Examples of natural zeolites are Analcime, Leucite, Pollucite, Wairakite, Bellbergite, Bikitaite, Boggsite, Brewsterite, Chabazite, Willhendersonite, Cowlesite, Dachiardite, Edingtonite, Epistilbite, Erionite, Faujasite, Ferrierite, Amicite, Garronite, Gismondine, Gobbinsite, Gmelinite, Gonnardite, Goosecreekite, Harmotome, Phillipsite, Wellsite, Clinoptilolite, Heulandite, Laumontite, Levyne, Mazzite, Merlinoite, Montesommaite, Mordenite, Mesolite, Natrolite, Scolecite, Offretite, Paranatrolite, Paulingite, Perlialite, Barrerite, Stilbite, Stellerite, Thomsonite, Tschernichite or Yugawaralite. Exemplary synthetic zeolites are zeolite A, zeolite X, zeolite Y, zeolite P, or the product ABSCENTS.

As zeolites, zeolites of the so called "medium" type can be used, in which the $SiO_2/AlO_2$ ratio is smaller than about 10, particularly the $SiO_2/AlO_2$ ratio of these zeolites may lie in a range of about 2 to about 10. Besides these "medium" zeolites, zeolites of the "high" type can furthermore be used, to which belong for example the known "molecular sieve" zeolites of the type ZSM. These "high" zeolites may be characterized by a $SiO_2/AlO_2$ ratio of at least about 35, such as by a $SiO_2/AlO_2$ ratio in a range of about 200 to about 500.

The naturally occurring spinals may be used as aluminates, in particular common spinal, zinc spinal, iron spinal or chromium spinal. Exemplary titanium dioxides are titanium dioxide in the rutile, anatase and brookite crystal forms, as well as iron-containing titanium dioxides such as, for example, ilmenite, calcium-containing titanium dioxide such as titanite or perowskite. Exemplary clay materials are those which are disclosed as clay materials in "Holleman and Wiberg, Lehrbuch der Anorganischen Chemie, Walter de Gruyter Verlag, $91^{st}$ to $100^{th}$ edition, 1985" on pages 783 to 785. Exemplary clay materials are kaolinite, illite, halloysite, montmorillonite and talc.

Exemplary carbon-containing, but not organic materials are those carbons which are cited as graphites in "Holleman and Wiberg, Lehrbuch der Anorganischen Chemie, Walter de Gruyter Verlag, $91^{st}$ to $100^{th}$ edition, 1985" on pages 705 to 708. Exemplary graphites are artificial graphites such as, for example, coke, pyrographite, active carbon or soot. In one aspect of the invention, when using the above-mentioned inorganic materials or mixtures thereof, these materials, in a quantity within a range from about 0.1 to about 1 wt %, such as in a quantity within a range from about 0.25 to about 0.75 wt %, and such as within a range from about 0.4 to about 0.6 wt %, based upon the total weight of the crosslinked polysaccharides, are brought into contact with the crosslinked polysaccharides.

According to one embodiment of the invention, the inorganic materials have a specific surface area determined according to the BET method within a range from about 30 to about 850 $m^2/g$, such as within a range from about 40 to about 500 $m^2/g$, such as within a range from about 100 to about 300 $m^2/g$, and such as within a range from about 150 to about 250 $m^2/g$. In general, and in the case that the inorganic materials are sipernates or aerosils, the surface area lies within a range from about 30 to about 850 $m^2/g$, such as within a range from about 40 to about 500 $m^2/g$, such as within a range from about 100 to about 300 $m^2/g$ and is determined using nitrogen in an Areameter according to ISO 5794, Annex D.

When using inorganic materials in the form of particles it is further exemplary that at least about 90 wt %, such as at least about 95 wt %, and such as at least about 99 wt % of the inorganic material has a particle size of less than about 200 μm, such as less than about 100 μm, and such as less than about 1 μm, and such as less than about 500 nm, and such as less than about 100 nm. The sipernates have a particle size within the range of about 10 to about 180 μm, such as within the range of about 20 to about 150 μm, and such as within the range from about 30 to about 110 μm. The sipernates have, in another embodiment of the process according to the invention, a particle size within the range from about 1 to about 40 μm, such as within the range from about 2 to about 30 μm, and such as within the range from about 3 to about 20 μm. These are respectively the average particle sizes determined according to the Multisizer Capillary Method according to ASTM C690-1992. Aerosils are characterized by a particle size within the range from about 5 to about 50 nm, such as within the range from about 8 to about 20 nm (such as "Aerosil 200" from Degussa AG). The particle size can be determined according to ASTM C690-1992 with a multisizer.

In one aspect of the invention, when using inorganic materials, the bringing into contact of the crosslinked polysaccharide with the inorganic material occurs in the presence of a "binding agent". This may be provided as a solution, when bringing it into contact. This solution may be an aqueous solution. As binding agent are considered all organic polymers which appear suitable to the skilled person. Exemplary polymers have a melting point according to ISO 11357 within the range from about −15 to about 150° C., such as within the range from about −12 to about 100° C., and such as within the range from about −9 to about 90° C. Polyethylene glycols may be used as binding agents.

The binding agents are present as a film in one aspect of the invention. This film may be located on the surface of the water-absorbing polysaccharide according to the invention. This film may have a thickness within the range from about 0.001 to about 20 nm, such as within the range from about 0.01 to about 15 nm, and such as within the range from about 0.1 to about 10 nm. The thickness can, for example, be measured by means of suitable microscopes. In this case, an average of at least about 10 sections should be formed. It is also possible that the film only covers part of the surface of the water-absorbing polysaccharide according to the invention. Usually suitable as binding agent are polymeric materials with a molecular weight of more than around 290 g/mol, which have a corresponding melting temperature and at a corresponding application temperature do not show any degradation or other change in molecular structure that would be disadvantageous for the sticking effect.

The number weight of the molecular weight ($M_n$) of the polymers which can be used as binding agent, determined by gel permeation chromatography (GPC), may lie within the range from about 290 and up to about 1,000,000, such as within the range from about 1,000 to about 100,000 and such as within the range from about 5,000 to about 20,000 g/mol. The molecular weight distribution of the cited polymers that can likewise be determined by gel permeation chromatography (GPC), can be monomodal. A polymer usable as binding agent can optionally also have a by- or higher modal distribution.

In a further aspect of the invention, when using binding agents, these are used in a quantity within a range from about 0.001 to about 10 wt %, such as from about 0.01 to about 5 wt %, and such as from about 0.05 to about 2.5 wt %, based upon the total weight of the crosslinked polysaccharide.

If using inorganic materials, optionally in combination with binding agents, these additional components can be brought into contact with the polysaccharides before the post-crosslinking, during the post-crosslinking or also after the post-crosslinking of the crosslinked polysaccharides, such as the addition of these components after the post-crosslinking. If the addition of the inorganic material and the binding agent occurs before the post-crosslinking of the crosslinked polysaccharides, the post-crosslinking and the adhesion of the inorganic material can be carried out at the same time by heating the polysaccharide to a temperature within the range from about 100 to about 160° C., such as from about 120 to about 140° C.

The invention also relates to a water-absorbent, at least partially neutralized polysaccharide which is obtainable by the above described process. The water-absorbing polysaccharide obtainable by the process according to the invention is characterized by an excellent absorption and retention capacity for water, aqueous solutions and body fluids. At the same time it has available, by means of the targeted crosslinking of the surfaces, a clearly improved absorption capacity for aqueous solution against an external pressure. The water-absorbing polysaccharide obtainable by the process according to the invention is, furthermore, stable upon storage, substantially free from residual monomer parts and organic solvents which frequently occur in the production of polyacrylates, only slightly soluble in aqueous liquids and, to high degree, biodegradable.

The present invention further relates to a particulate, water-absorbent polysaccharide, whereby the polysaccharide is crosslinked with a polyphosphate or with polyphosphoric acid in a quantity within a range from about 0.001 to about 20 wt %, such as in a quantity within a range from about 0.01 to about 10 wt %, and such as in a quantity within a range from about 0.05 to about 5 wt %, respectively based upon the weight of the polysaccharide. The invention additionally relates, in a further embodiment, to a particulate water-absorbent polysaccharide, with at least about 5 wt %, and such as at least about 90 wt %, respectively based upon the water-absorbent polysaccharide, of a branched polysaccharide, such as cellulose and/or derivatives thereof, whereby the water-absorbing polysaccharide has a surface part coated with an inorganic particle. In an additional aspect, the water-absorbent polysaccharide according to the invention also has a binding agent at least in the surface part. The water-absorbent polysaccharide according to the invention has inorganic particles, for example, in a quantity within the range from about 0.001 to about 20 wt %, such as within the range from about 0.01 to about 10 wt %, respectively based upon the water-absorbent polysaccharide according to the invention. Independent thereof, the water-absorbent polysaccharide according to the invention has binding agent, for example, in a quantity within the range from about 0.001 to about 20 wt %, such as within the range from about 0.01 to about 10 wt %, respectively based upon the water-absorbent polysaccharide according to the invention. In one aspect of the invention, those polysaccharides which have already been cited in connection with the process according to the invention for producing a water-absorbent polysaccharide are utilized, whereby the same is also true for inorganic particles and for binding agents.

In one embodiment, the water-absorbent polysaccharide according to the invention is present in an average particle diameter determined according to ERT 420.1-99 within a range from about 1 to about 2,000 μm, such as within a range from about 100 to about 1,000 μm, and such as within a range from about 150 to about 850 μm. In another aspect of the invention, at least about 50 wt %, such as at least about 75 wt %, and such as at least about 100 wt % of the water-absorbent polysaccharide according to the invention has a particle size determined by sieve analysis within the range from about 300 to about 600 μm.

In a further aspect of the invention, the particulate water-absorbent polysaccharide according to the invention has at least one, such as all of the following properties:

($\alpha$1) an AUL value determined according to the herein-described test method at a pressure of about 0.9 psi within a range from about 10 to about 22 g/g, such as within a range from about 12 to about 19 g/g, and such as within a range from about 14 to about 17 g/g at a CRC value determined according to the herein-described test method within a range from about 15 to about 20 g/g;

($\alpha$2) an AUL value at a pressure of about 0.9 psi determined according to the herein-described test method within a range from about 6 to about 20 g/g, such as within a range from about 8 to about 17 g/g, and such as within a range from about 10 to about 14 g/g at a CRC value determined according to the herein-described test method within a range from about 20 to about 25 g/g;

($\alpha$3) an AUL value at a pressure of about 0.9 psi determined according to the herein-described test method within a range from about 6 to about 15 g/g, such as within a range from about 7 to about 12 g/g, and such as within a range from about 8 to about 10 g/g at a CRC value determined according to the herein-described test method within a range from about 25 to about 30 g/g;

($\alpha$4) an AUL value at a pressure of about 0.9 psi determined according to the herein-described test method within a range from about 5 to about 12 g/g, such as within a range from about 6 to about 10 g/g, and such as within a range from about 7 to about 9 g/g at a CRC value determined according to the herein-described test method of more than about 30 g/g.

In principle, each of the above figures or a combination thereof represents an embodiment of the present invention. Exemplary particulate water-absorbent polysaccharides according to the invention are those which are characterized by the following properties or property combinations: $\alpha$1, $\alpha$2, $\alpha$3, $\alpha$4, $\alpha$5, $\alpha$6, $\alpha$1$\alpha$2, $\alpha$1$\alpha$3, $\alpha$1$\alpha$4, $\alpha$2$\alpha$3, $\alpha$2$\alpha$4, $\alpha$3$\alpha$4, $\alpha$1$\alpha$2$\alpha$3, $\alpha$1$\alpha$3$\alpha$4, $\alpha$2$\alpha$3$\alpha$4, $\alpha$1$\alpha$2$\alpha$3$\alpha$4.

In a further aspect of the invention, the particulate water-absorbent polysaccharides have at least one, such as all of the following properties:

($\beta$1) a biodegradability determined according to the herein-described test method of at least about 40% in about 90 days, such as at least about 50% in about 90 days, and such as at least about 65% in about 90 days, and such as at least about 75% in about 90 days;

($\beta$2) an extractable part determined according to ERT 470.2-99 within a range from about 5 to about 60%, such as within a range from about 8 to about 30%, and such as within a range from about 10 to about 20%;

($\beta$3) a value for the Gel Bed Permeability determined according to the herein-described test method within a range from about 1 to about $500 \times 10^{-9}$ cm$^2$, such as within a range from about 5 to about $300 \times 10^{-9}$ cm$^2$, and such as within a range from about 20 to $200 \times 10^{-9}$ cm$^2$. In principle, each of the above figures or a combination thereof represents an embodiment of the present invention.

Exemplary particulate water-absorbent polysaccharides according to the invention are those which are characterized by the following properties or property combinations: $\beta$1, $\beta$2, $\beta$3, $\beta$1$\beta$2, $\beta$1$\beta$3, $\beta$2$\beta$3, $\beta$1$\beta$2$\beta$3. In another embodiment of the water-absorbed polysaccharide according to the invention, a biodegradability determined according to the herein-described test method is present within a range from about 25 to about 50% in about 45 days and within a range from more than about 50 to about 90% in about 90 days, such as at least about 28% in about 45 days and of at least about 51% in about 90 days.

It is further exemplary in connection with the particulate water-absorbing, at least partially neutralized polysaccharides according to the invention, that these have a "sliminess" determined according to the herein-described test method, within a range from about 1 to about 3, such as within a range from about 1 to about 2, and such as about 1. It is further exemplary that the particulate water-absorbent polysaccharides according to the invention have an inner part and an outer part surrounding the inner part, whereby the outer part has a higher degree of crosslinking than the inner part, such that a core-shell structure may be formed. The increased crosslinking in the outer part of the crosslinked polysaccharides may be achieved by post-crosslinking of reactive groups near the surface. In one aspect, polyphosphates and polyphosphoric acids are used as post-crosslinker for the post-crosslinking, whereby those polyphosphates and polyphosphoric acids are exemplary which have already been cited in connection with the first process step of the process according to the invention for producing water-absorbent polysaccharides. As outer part of the particle is understood each volume element of the particle whose distance from the center of the particle is at least about 75%, such as at least about 85%, and such as at least about 95% of the outer radius of the polymer particle.

The invention further relates to a composite comprising an above-defined water-absorbent polysaccharide and a substrate. In one aspect, the water-absorbent polysaccharide according to the invention and the substrate are firmly bound together. Sheets made from polymers may be used as a substrate, for example, from polyethylene, polypropylene or polyamide, metals, non-woven materials, fluff, tissues, woven materials, natural or synthetic fibres, or other foams. According to the invention, as composite may be sealant materials, cables, absorbent cores as well as diapers and hygiene articles comprising these. The invention further relates to a process for producing a composite, wherein a water-absorbent polysaccharide according to the invention and a substrate and optionally a suitable additive are brought into contact with each other. In one aspect, the bringing into contact occurs by wetlaid and airlaid processes, compacting, extruding and mixing.

The invention additionally relates to a composite which is obtainable by the above process. The invention further relates to chemical products, in particular foams, formed bodies, fibres, sheets, films, cables, sealant materials, liquid-absorbing hygiene articles, carriers for plant or fungus growth-regulating agents or plant protection agents, additives for construction materials, packaging materials or soil additives, which comprise the water-absorbent polysaccharide according to the invention for the above-described composite. These chemical products are distinguished in particular by a particularly good biodegradability.

In addition, the invention relates to the use of the water-absorbent polysaccharides according to the invention or of the above-described composite in hygiene products, for combating floods, for insulating against water, for regulating the water balance of soils or for treatment of food products. The invention also relates to the use of polyphosphate or polyphosphoric acid for crosslinking of an uncrosslinked polysaccharide, wherein those polyphosphates, polyphosphoric acids and polysaccharides are exemplary which have already been cited in connection with the first process step of the process according to the invention for producing water-absorbent polysaccharides.

The invention is now more closely described by means of test methods and non-limiting examples.

Test Methods

Determination of the Gel Bed Permeability (GBP)

This property is determined according to the test methods disclosed in U.S. Pat. No. 6,387,495 that similarly reads as follows.

Figure 2:
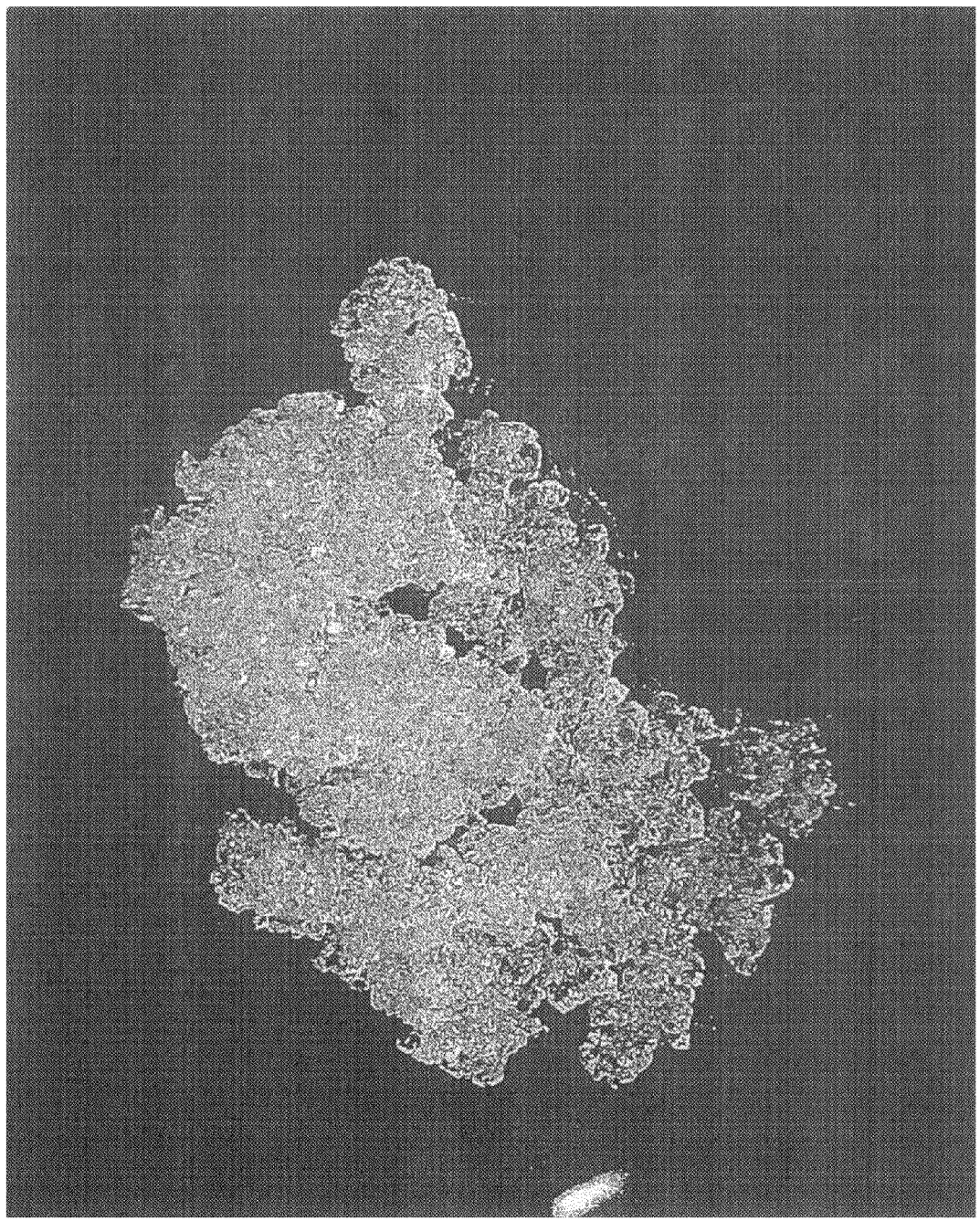
FIG. 2 is a picture of individual gel particles that stick together.

A suitable piston/cylinder apparatus for performing the Gel Bed Permeability (GBP) test is shown in FIGS. 1 and 2. Referring to FIG. 1, an apparatus (120) consists of a cylinder (122) and a piston (generally indicated as 124). As shown in FIG. 1, the piston (124) consists of a cylindrical LEXAN® shaft (126) having a concentric cylindrical hole (128) bored down the longitudinal axis of the shaft. Both ends of the shaft (126) are machined to provide first and second ends (130, 132). A weight (134) rests on the first end (130) and has a cylindrical hole (136) bored through the center thereof. Inserted on the second end (132) is a circular piston head (140). The piston head (140) is sized so as to vertically move inside the cylinder (122). As shown in FIG. 2, the piston head (140) is provided with inner and outer concentric rings containing seven and fourteen approximately 0.375 inch (0.95 cm) cylindrical holes, respectively (indicated generally by arrows 142 and 144). The holes in each of these concentric rings are bored from the top to bottom of the piston head (140). The piston head (140) also has a cylindrical hole (146) bored in the center thereof to receive the second end (132) of the shaft (126).

Attached to the bottom end of the cylinder (122) is a No. 400 mesh stainless steel cloth screen (148) that is biaxially stretched to tautness prior to attachment. Attached to the bottom end of the piston head (140) is a No. 400 mesh stainless steel cloth screen (150) that is biaxially stretched to tautness prior to attachment. A sample of adsorbent material (152) is supported on the screen (148).

The cylinder (122) is bored from a transparent LEXAN® rod or equivalent and has an inner diameter of 6.00 cm (area=28.27 cm$^2$), a wall thickness of approximately 0.5 cm, and a height of approximately 5.0 cm. The piston head (140) is machined from a LEXAN® rod. It has a height of approximately 0.625 inches (1.59 cm) and a diameter sized such that it fits within the cylinder (122) with minimum wall clearances, but still slides freely. A hole (146) in the center of the piston head (140) has a threaded 0.625 inch (1.59 cm) opening (18 threads/inch) for the second end (132) of the shaft (126). The shaft (126) is machined from a LEXAN® rod and has an outer diameter of 0.875 inches (2.22 cm) and an inner diameter of 0.250 inches (0.64 cm). The second end (132) is approximately 0.5 inches (1.27 cm) long and is threaded to match the hole (146) in the piston head (140). The first end (130) is approximately 1 inch (2.54 cm) long and 0.623 inches (1.58 cm) in diameter, forming an annular shoulder to support the stainless steel weight (134). The annular stainless steel weight (134) has an inner diameter of 0.625 inches (1.59 cm), so that it slips onto the first end (130) of the shaft (126) and rests on the annular shoulder formed therein. The combined weight of the piston (124) and the weight (134) equals approximately 596 g, which corresponds to a pressure of 0.30 psi (20,685 dynes/cm.sup.2), for an area of 28.27 cm$^2$.

When fluids flow through the piston/cylinder apparatus, the cylinder (122) generally rests on a 16-mesh, rigid stainless-steel support screen (not shown) or equivalent.

The piston and weight are placed in an empty cylinder to obtain a measurement from the bottom of the weight to the top of the cylinder. This measurement is taken using a caliper readable to 0.01 mm. This measurement will later be used to calculate the height of the bed of the sample of adsorbent material (152). It is important to measure each cylinder empty and keep track of which piston and weight were used. The same piston and weight should be used for measurement when the sample of adsorbent material is swollen.

The absorbent layer used for GBP measurements is formed by swelling approximately 0.9 g of a sample of adsorbent material in the GBP cylinder apparatus (dry adsorbent material should be spread evenly over the screen of the cylinder prior to swelling) with a fluid, typically 0.9% (w/v) aqueous NaCl, for a time period of approximately 15 minutes. The sample of adsorbent material is taken from a population of adsorbent material that is prescreened through US standard 30 mesh and retained on US standard 50 mesh. The adsorbent material, therefore, has a particle size of between 300 and 600 microns. The particles may be prescreened by hand or automatically prescreened with, for example, a Ro-Tap Mechanical Sieve Shaker Model B, commercially available from W. S. Tyler, Inc., Mentor, Ohio USA.

At the end of the 15 minute period, the cylinder is removed from the fluid and the piston/weight assembly is placed on the sample of adsorbent material. The thickness of the swollen sample of adsorbent material is determined by measuring from the bottom of the weight to top of the cylinder with a micrometer. The value obtained when taking this measurement with the empty cylinder is subtracted from the value obtained after swelling the sample of adsorbent material. The resulting value is the height of the bed of the swollen sample of adsorbent material, H.

The GBP measurement is initiated by adding the fluid to the cylinder (122) until the fluid attains a height of 4.0 cm above the bottom of the sample of adsorbent material (152). This fluid height is maintained throughout the test. The quantity of fluid passing through the sample of adsorbent material (152) versus time is measured gravimetrically. Data points are collected every second for the first two minutes of the test and every two seconds for the remainder. When the data are plotted as quantity of fluid passing through the bed of the sample of adsorbent material versus time, it becomes clear to one skilled in the art when a steady flow rate has been attained. Only data collected once the flow rate has become steady is used in the flow rate calculation. The flow rate, Q, through the sample of adsorbent material (152), is determined in units of g/s by a linear least-square fit of fluid passing through the sample of adsorbent material (in grams) versus time (in seconds).

Permeability in $cm^2$ is obtained by the following equation:

$$K=[Q*(H*Mu)]/[A*Rho*P]$$

Where K=Gel Bed Permeability ($cm^2$); Q=flow rate (g/sec); H=height of bed of sample of adsorbent material (cm); Mu=liquid viscosity (poise); A=cross-sectional area for liquid flow ($cm^2$); Rho=liquid density ($g/cm^3$); and P=hydrostatic pressure ($dynes/cm^2$) (normally approximately 3,923 $dynes/cm^2$).

Determination of the Centrifugal Retention Capacity (CRC)

This property is determined according to the test methods disclosed in EP 0 601 529 B1 as similarly reproduced below.

As used herein, the Centrifugal Retention Capacity (CRC) is a measure of the absorbent capacity of the superabsorbent material retained after being subjected to centrifugation under controlled conditions. The superabsorbent sample to be tested is taken from superabsorbent material which is pre-screened through U.S. standard #30 mesh and retained on U.S. standard #50 mesh. The superabsorbent material therefore has a particle size of between 300 and 600 microns. The particles can be prescreened by hand or automatically as described above for the AUL. The CRC can be measured by placing 0.200 grams of the sample material to be tested (moisture content of less than 5 weight percent) into a water-permeable bag which will contain the sample while allowing the test solution (0.9 percent NaCl solution) to be freely absorbed by the sample. A heat-sealable tea bag material (grade 542, commercially available from Kimberly-Clark Corporation, Neenah, Wis.) works well for most applications. The bag is formed by folding a 5 inches by 3 inches sample of the bag material in half and heat sealing two of the open edges to form a 2.5×3 inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. Three sample bags are tested for each superabsorbent material.

Determination of the Absorption Under Load at 0.9 psi (AUL at 0.9 psi)

This property is determined according to the test methods disclosed in EP 0 339 461 B1, wherein the following loads cited in the tables were used.

Figure 3:
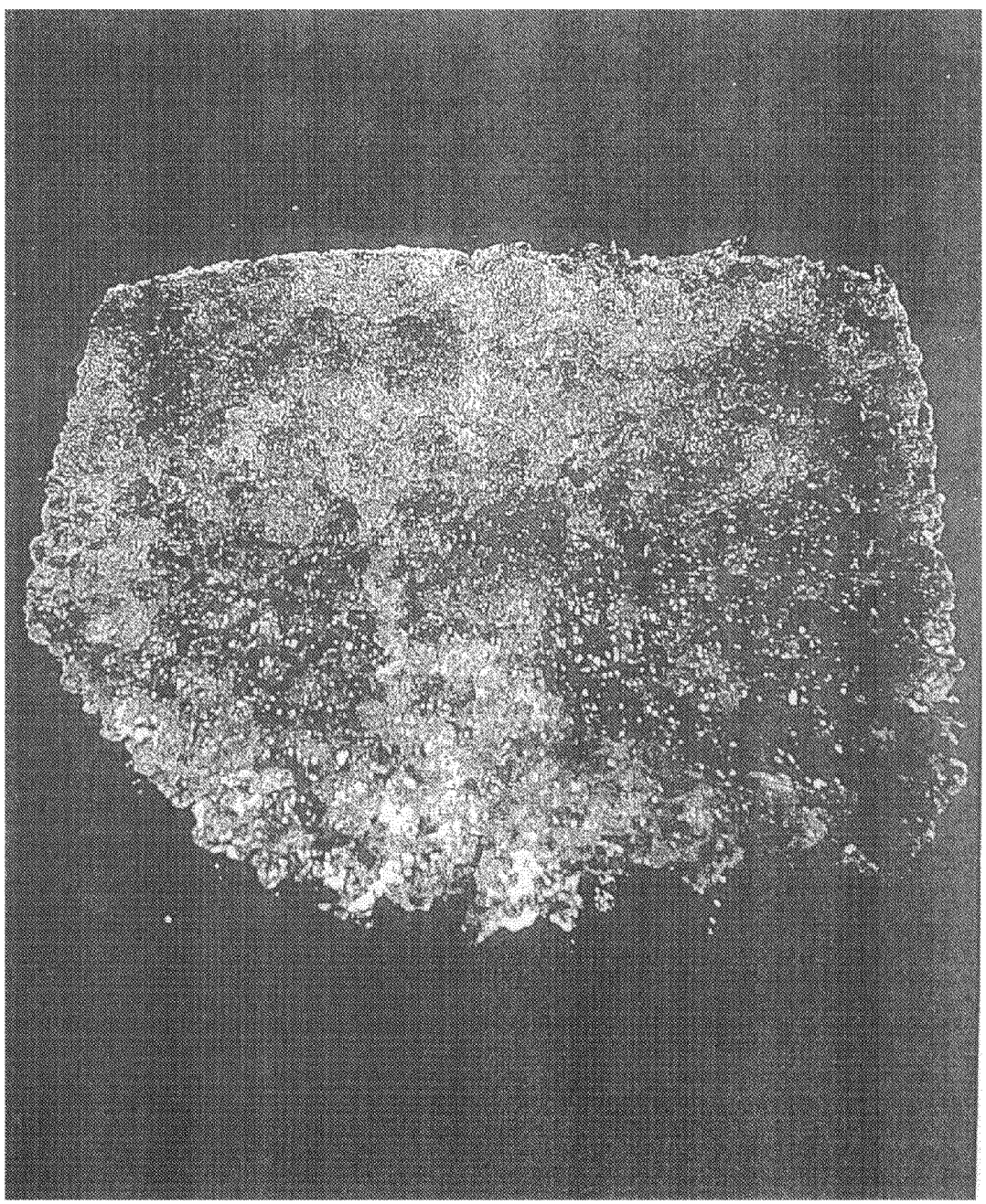
FIG. 3 is a picture of a gel layer with gel particles and stick together.

Referring to FIG. 3, a Demand Absorbency Tester (DAT) 48 is used, which is similar to a GATS (Gravimetric Absorbency Test System), available from M/K Systems, Danners, Ma., as well as the system described by Lichstein in pages 129-142 of the INDA Technological Symposium Proceedings, March 1974. A porous plate 57 is used having ports 52 confined within the 2.5 cm. diameter area and covered by the absorbency under load (AUL) apparatus 50. An electro balance 54 is used to measure the flow of fluid, normally 0.9 (w/w) % NaCl into the hydrocolloid particles 66. The special apparatus 50 used to contain the hydrocolloid particles is made from one inch (2.54 cm.) inside diameter thermoplastic tubing 56 machined-out slightly to be sure of concentricity and then 100 mesh stainless steel wire cloth 58 is fused on the bottom by heating the wire cloth in a flame until red hot after which the cylinder is held onto the cloth until cooled. A soldering iron can be utilized to touch up the seal if unsuccessful or it breaks. Care must be taken to maintain a flat smooth bottom and not distort the inside of the cylinder. The 4.4 g piston (60) is made from one inch diameter solid material (e.g., Plexiglas) and is machined to closely fit without binding in the cylinder 56. A standard 100 gm. weight 62 is used to provide a 21,000 dyne/sq.cm. (about 0.3 psi) restraining load which is commonly experienced in infant diapers. Unless specified otherwise, a sample corresponding to a layer of at least about 300 gsm. (0.16 g.) of granules is utilized for testing AUL. The sample is taken from granules which are pre-screened through U.S. standard #30 mesh and retained on U.S. std. #50 mesh. The particles can be pre-screened by hand or automatically with, for example, a Ro-Tap Mechanical Sieve Shaker Model B available from W. S. Tyler, Inc., Mentor Ohio.

This test is initiated by placing a 3 cm. diameter GF/A glass filter paper 64 onto the plate 57, (the paper is sized to be larger than the i.d. and smaller than the o.d. of the cylinder, to insure good contact while eliminating evaporation over the ports 52 of the DAT 48 and then allowing saturation to occur. The desired amount of particles 66 (about 0.16 g.) is weighed out on a weigh paper and placed on the wire cloth 58 at the bottom of the AUL apparatus 50. The apparatus 50 is shaken to level the granules 66 on the wire cloth 58. Care is taken to be sure no granules 66 are clinging to the wall of the cylinder 56. After carefully placing the piston 60 and weight 62 on the granules 66 in the cylinder 56, the AUL apparatus 50 is placed on the glass filter paper 64. The amount of fluid pick-up is monitored as a function of time either directly by hand, with a strip chart recorder or directly into a data acquisition or Personal Computer System.

The amount of fluid pickup measured after one hour is the AUL value, however, the rate of fluid pickup can also be measured. Two checks can be made to insure the accuracy of the instantaneous final readout. The height the piston 60 rises multiplied by the cross-sectional area of the cylinder 56 should nearly equal the amount of fluid picked up and the cylinder apparatus 50 can be weighed before and after the test, with the difference in weight equaling the fluid pick-up.

To analyze the impact of different restraining loads additional or smaller weights are utilized. Further insights are also obtained by analyzing the actual work done which is simply the height multiplied by the restraining load (or the restraining pressure in dynes/sq.cm. multiplied by the AUL (ml./g.) to yield the amount of work (ergs./g.). This is the total work done due to the particles 66 being totally restrained from moving in the X-Y plane by the cylinder 56. This restraint in the X-Y plane is the key feature of this test, since with a 300 gsm. layer the particles being restrained in the X-Y plane must expand a significant distance vertically against the restraining load in order to obtain a large AUL value.

Determination of the Sliminess

The swollen gel obtained in the determination of the CRC was evaluated in daylight by vision inspection and given the following marks according to the optical impression. Reference is further made for clarification to the pictures accompanying the individual marks.

Figure 4:
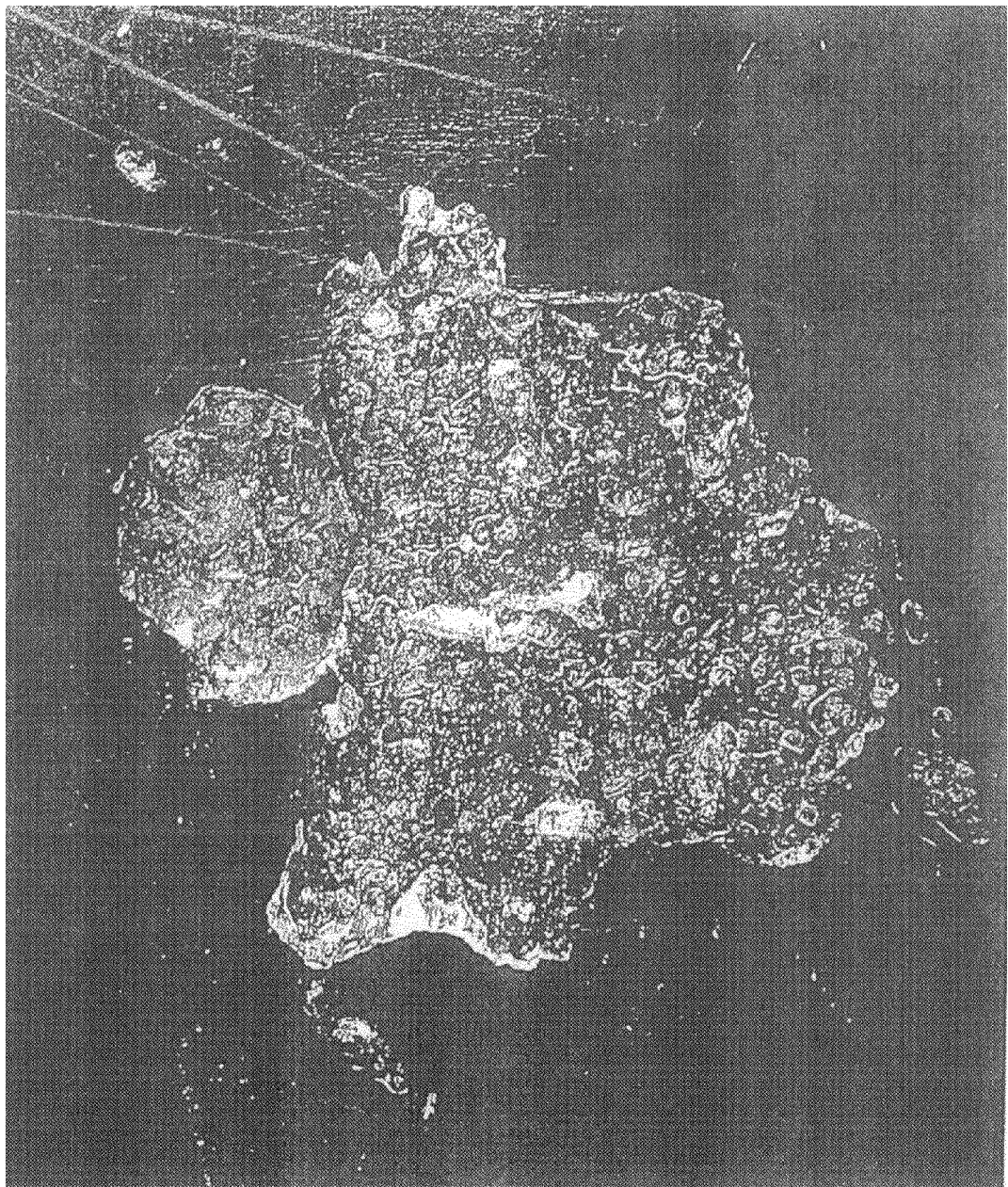
FIG. 4 is a picture of a gel sheet with gel particles.
Figure 5:
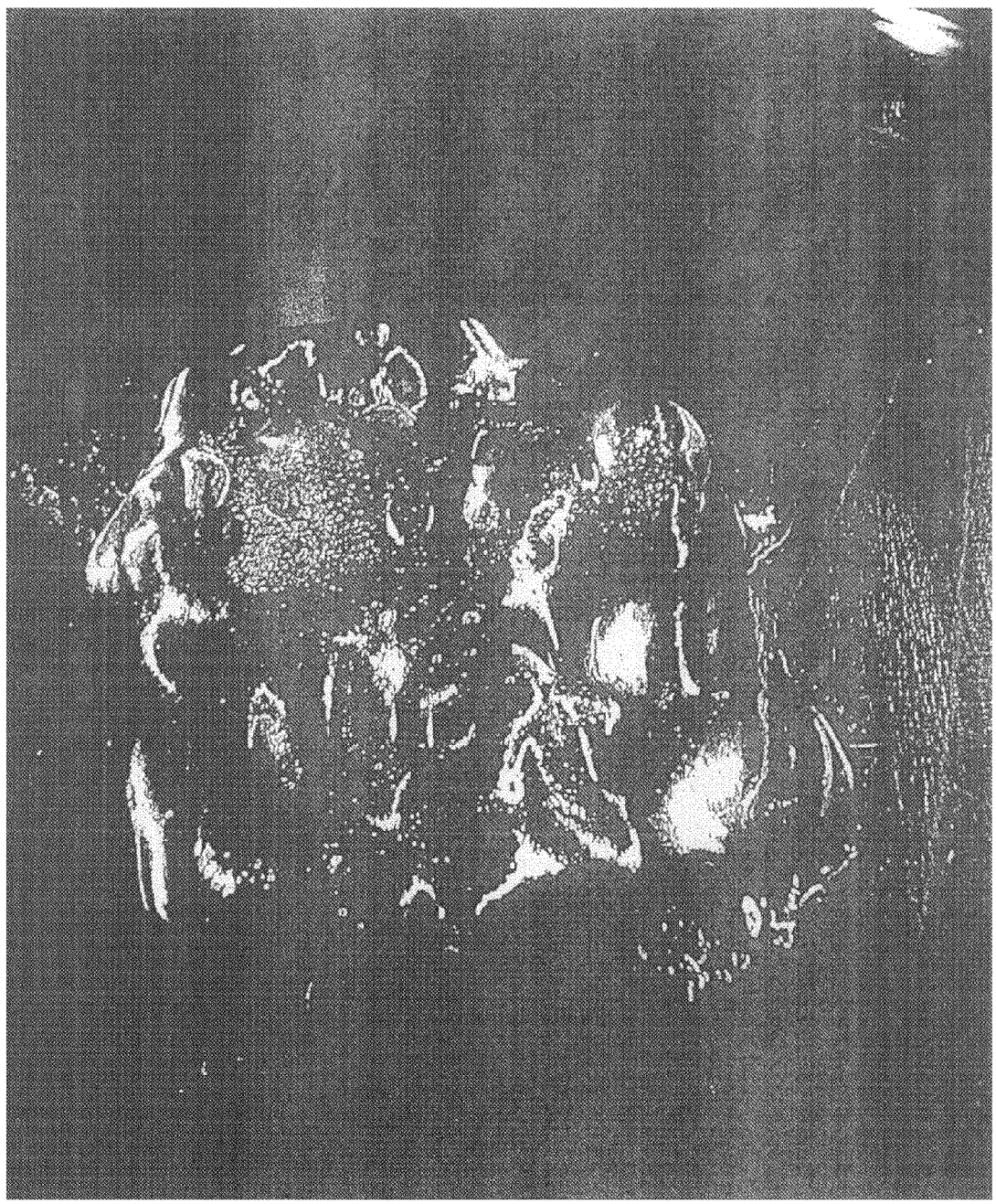
FIG. 5 is a picture of paste.
Figure 6:
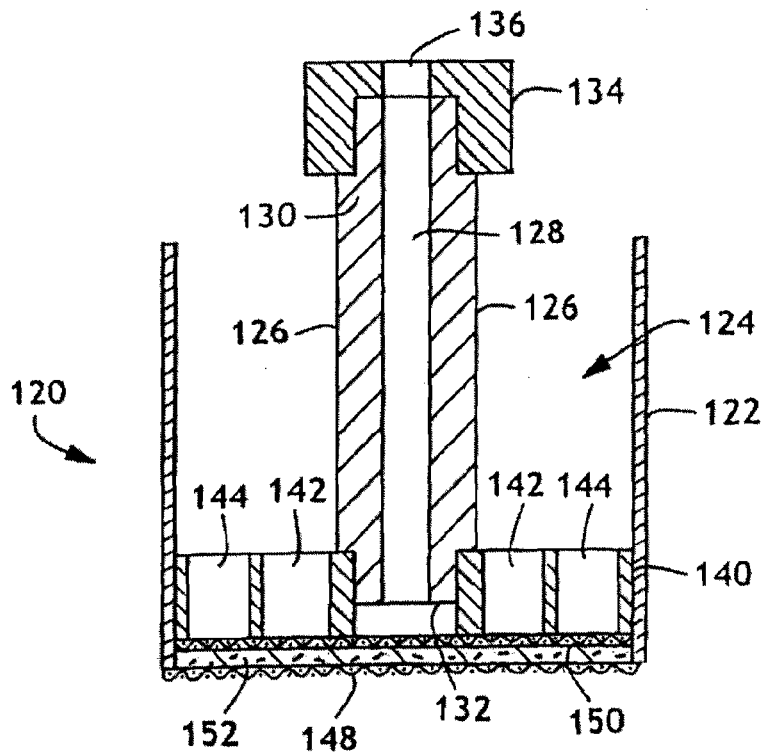
FIG. 6 illustrates an apparatus used suitable for measuring Gel Bed Permeability.
Figure 7:
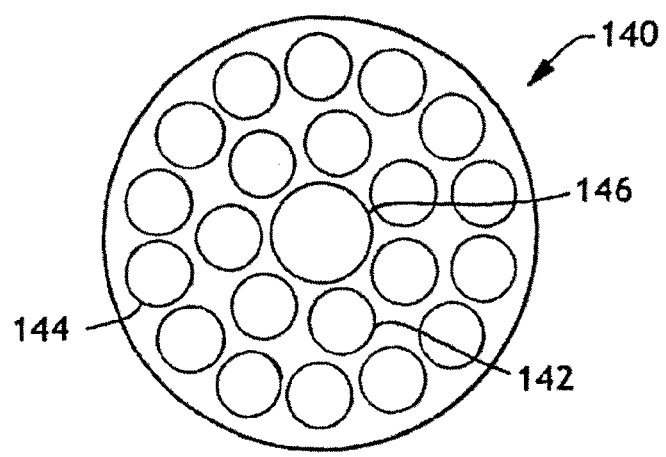
FIG. 7 illustrates a bottom plan view of the apparatus illustrated in FIG. 6.
Figure 8:
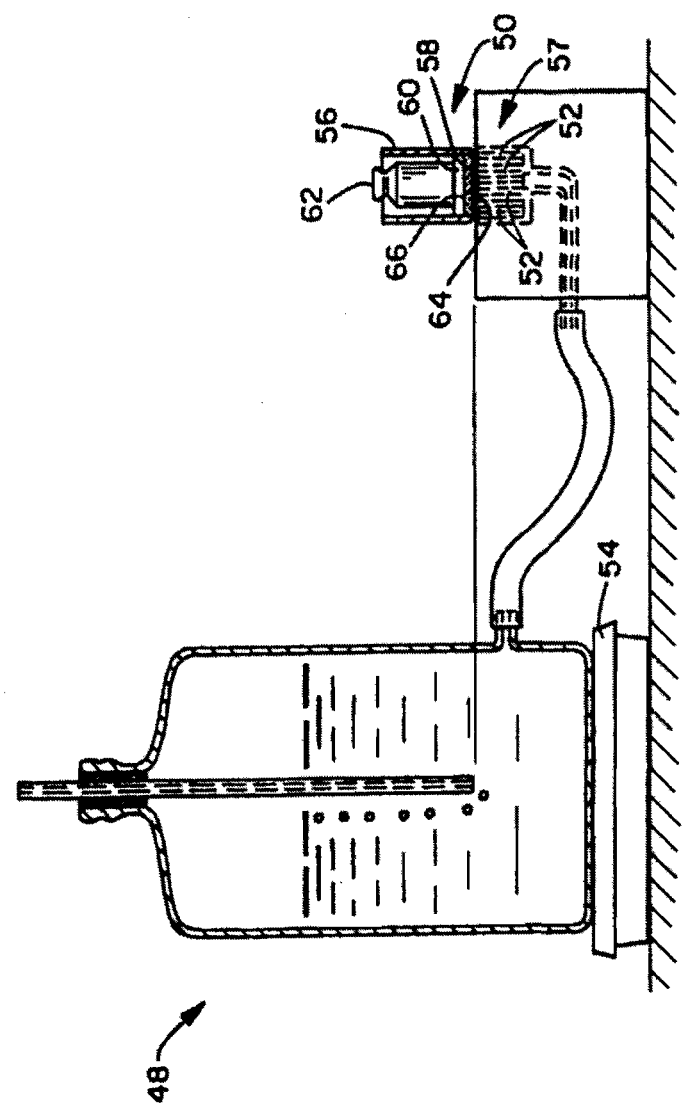
FIG. 8 is a side elevational view of an apparatus used to measure the absorbency of fluid by superabsorbent particles against an applied restraint.

| Mark | Optical impression |
|---|---|
| 1 | Individual gel particles are clearly separated from each other and do not stick together. See FIG. 1 |
| 2 | Individual gel particles are clearly separated from each other and stick together slightly. See FIG. 2 |
| 3 | Gel layer with gel particles which stick to each other strongly and are hardly separated from each other. See FIG. 3 |
| 4 | Gel sheet with gel particles no longer distinguishable. See FIG. 4 |
| 5 | Paste-like, flowing. See FIG. 5 |

Determination of the Biodegradability

The biodegradability (mineralization) is determined by the Controlled Composting Test (according to ISO 14855, ASTM D5338-92, DIN V54900-2).

Example 1A

Polyphosphoric acid (84% from the company Clariant, Germany) in a quantity of 0.09 wt. %, based upon the amount of sodium carboxymethyl cellulose used, was dissolved in distilled water and the pH value adjusted with sodium hydroxide to 11.5. The sodium carboxymethylcellulose (Cekol® 100,000 from the company Noviant, Netherlands, with an active substance content of 15 wt. %) was homogeneously kneaded into the solution and then chopped ("wolfed"). The chopped gel was then dried at temperatures of 120° C. for 150 minutes and then milled to a particle size within a range from 850 μm to 150 μm. A powder A1 was obtained.

Example 1B

An aqueous solution with a pH of 11.0 comprising 6 wt. %, based upon the total weight of the aqueous solution, of polyphosphoric acid as post-crosslinker, is brought into contact with powder A1 in an amount of 10 wt. %, based upon the total weight of powder A1. The coated pre-product is heated at temperatures of 130° C. for a duration of 50 minutes. A powder B1 is obtained. The powders A1 and B1 were characterized by the following properties:

TABLE 1

| powder | CRC [g/g] | $AUL_{0.3\,psi}$ [g/g] | $AUL_{0.9\,psi}$ [g/g] | GBP | sliminess |
|---|---|---|---|---|---|
| A1 | 30.8 | | | | |
| B1 | 19.2 | 20.3 | 15.6 | 57 | 1 |

Example 2A

Example 1A was repeated, wherein in the place of 0.09 wt %, based upon the amount of sodium carboxymethylcellulose used, 0.1 wt % of polyphosphoric acid (84%, from the company Clariant, Germany) was used. A powder A2 is obtained.

Example 2B

Example 1B was repeated, wherein the aqueous solution with a pH of 11.0 additionally comprised 0.3 wt %, based upon the amount of powder A2, Aerosil 200 from Degussa AG, Germany, and 5 wt. % of polyphosphoric acid, based upon the total weight of the aqueous solution, was used and heated at 125° C. for 65 minutes. A powder B2 is obtained. The powders A2 and B2 were characterized by the following properties:

TABLE 2

| Powder | CRC [g/g] | $AUL_{0.3\,psi}$ [g/g] | $AUL_{0.9\,psi}$ [g/g] | GBP | Sliminess |
|---|---|---|---|---|---|
| A2 | 28.5 | | | | |
| B2 | 19.0 | 20.4 | 14.3 | 223 | 1 |

Example 3A

Example 1A was repeated, whereby instead of Cecol®, 100,000, Cecol® 50,000 was used. A powder A3 is obtained.

Example 3B

Example 1B was repeated, wherein the aqueous solution with a pH of 11.0 additionally comprised 0.3 wt. %, based upon the amount of powder A3, of Aerosil 200 of Degussa AG, Germany. In addition, drying was carried out at 130° C. for 110 minutes. A powder B3 is obtained. The powders A3 and B3 were characterized by the following properties:

TABLE 3

| Powder | CRC [g/g] | $AUL_{0.3\,psi}$ [g/g] | $AUL_{0.9\,psi}$ [g/g] | GBP | Sliminess |
|---|---|---|---|---|---|
| A3 | 52.8 | | | | |
| B3 | 20.6 | 20.7 | 14.6 | 142 | 1 |

Example 4A

Example 1A was repeated, whereby instead of 0.09 wt. %, based upon the amount of sodium carboxymethylcellulose used, 0.1 wt.-% polyphosphoric acid (84%, from the company Clariant, Germany) was used. A powder A4 is obtained.

Example 4B

Example 1B was repeated, wherein the aqueous solution with a pH of 11.0 additionally comprised 0.5 wt. %, based upon the amount of powder A4, of Sipernat 22S of Degussa AG, Germany and wherein it was heated at 125° C. for 65 minutes. A powder B4 is obtained. The powders A4 and B4 were characterized by the following properties:

TABLE 4

| Powder | CRC [g/g] | $AUL_{0.3\,psi}$ [g/g] | $AUL_{0.9\,psi}$ [g/g] | GBP | Sliminess |
|---|---|---|---|---|---|
| A4 | 32.9 | | | | |
| B4 | 19.0 | 19.9 | 15.2 | 411 | 1 |

The invention claimed is:

1. A process for producing a particulate water-absorbent polycarboxypolysaccharide wherein said water-absorbent polycarboxypolysaccharide is chemically modified with an average degree of carboxyl substitution within the range from 0.4 to about 1.5 and has a ($\alpha$1) an absorption under load value at a pressure of 0.9 psi within a range from 10 to 22 g/g with a centrifuge retention capacity value within a range from 15 to 20 g/g; or ($\alpha$2) an absorption under load value at a pressure of 0.9 psi within a range from 6 to 20 g/g with a centrifuge retention capacity value within a range from 20 to 25 g/g, the process comprising the steps of:
   a) preparing an aqueous solution having a pH of from about 8 to about 12 by mixing a polycarboxypolysaccharide with a crosslinking agent consisting essentially of polyphosphoric acid in an amount within a range from 0.001 to 20 wt. %, based upon the weight of the polycarboxypolysaccharide, in the presence of water to form said water-absorbent polycarboxypolysaccharide, wherein the mixing step occurs in a kneader wherein the kneader has at least two kneading shafts; and
   b) drying the water-absorbent polycarboxypolysaccharide gel on a belt drier at a temperature of from about 120° C. to about 130° C. for a time period of from about 50 minutes to about 150 minutes.

2. The process according to claim 1, wherein the at least two kneader shafts have a contour which at least partially reaches into each other.

3. The process according to claim 1, wherein the at least two kneader shafts form a conveying channel running at least partially axial to one of the knead shafts.

4. The process according to claim 1, wherein the carboxyl groups of the uncrosslinked polycarboxypolysaccharide are neutralized to at least about 50 mol %.

5. The process according to claim 1, wherein the crosslinking or the drying occurs at a temperature above about 70° C.

6. The process according to claim 1, wherein the mixing step of the polycarboxypolysaccharide with the crosslinking agent occurs in the absence of an organic solvent.

7. The process according to claim 1, wherein the water-absorbent polycarboxypolysaccharide comprises a salt content of less than about 20 wt. %, based upon the total weight of the polycarboxypolysaccharide.

8. The process according to claim 1, wherein the polyphosphate comprises as crosslinking agent the composition $M_{n+2}^I[P_nO_{3n+1}]$ or $M_n^I[H_2P_nO_{3n+1}]$, wherein $M^I$ is a monovalent metal and n has a value of at least 2.

9. The process according to claim 1, wherein the polyphosphoric acid as crosslinking agent has the composition $H_{n+2}P_nO_{3n+1}$ or $(HPO_3)_n$, in which n has a value of at least 2.

10. The process according to claim 1, wherein the polycarboxypolysaccharide gel is comminuted before the drying and/or wherein the dried, crosslinking polysaccharide is milled, so that particulate, crosslinked polycarboxypolysaccharides are obtained.

11. The process according to claim 10, wherein the particulate, crosslinked polycarboxypolysaccharide is post-crosslinked in the outer part of the particle with a post-crosslinking agent.

12. The process according to claim 11, wherein the post-crosslinking agent is used in the form of about 0.01 to about 80 wt. % aqueous solution.

13. The process according to claim 11, wherein the post-crosslinking agent is a polyphosphate or polyphosphoric acid.

14. The process according to claim 11, wherein the post-crosslinking of the crosslinked polycarboxypolysaccharides with the post-crosslinking agent occurs in the presence of inorganic particles.

15. A particulate, water-absorbent polycarboxypolysaccharide obtainable by a process for producing the particulate water-absorbent polycarboxypolysaccharide wherein said water-absorbent polycarboxypolysaccharide is chemically modified with an average degree of carboxyl substitution within the range from 0.4 to about 1.5 and has a ($\alpha$1) an absorption under load value at a pressure of 0.9 psi within a range from 10 to 22 g/g with a centrifuge retention capacity value within a range from 15 to 20 g/g; or ($\alpha$2) an absorption under load value at a pressure of 0.9 psi within a range from 6 to 20 g/g with a centrifuge retention capacity value within a range from 20 to 25 g/g, the process comprising the process steps of:
   a) preparing an aqueous solution having a pH of from about 8 to about 12 by mixing a polycarboxypolysaccharide with a crosslinking agent consisting essentially of polyphosphoric acid in an amount within a range from 0.001 to 20 wt. %, based upon the weight of the polycarboxypolysaccharide, in the presence of water to form the water-absorbent polycarboxypolysaccharide gel wherein the mixing step occurs in a kneader wherein the kneader has at least two kneading shafts; and
   b) drying the water-absorbent polycarboxypolysaccharide gel on a belt drier at a temperature of from about 120° C. to about 130° C. for a time period of from about 50 minutes to about 150 minutes.

16. The particulate, water-absorbent polycarboxypolysaccharide according to claim 15, wherein the polysaccharide is an at least partially neutralized polycarboxypolysaccharide.

17. The particulate, water-absorbent polycarboxypolysaccharide according to claim 15, wherein the polycarboxypolysaccharide is present in particulate form with a particle diameter within a range from 150 to 850 μm.

18. The particulate, water-absorbent polycarboxypolysaccharide according to claim 15, wherein the particulate, water-absorbent polycarboxypolysaccharide has a Gel Bed Permeability of from about $20\times10^{-9}$ $cm^2$ to $500\times10^{-9}$ $cm^2$.

19. A composite comprising a water-absorbent, at least partially neutralized polycarboxypolysaccharide according to claim 15 and a substrate.

* * * * *

UNITED STATES PATENT AND TRADEMARK OFFICE
CERTIFICATE OF CORRECTION

PATENT NO. : 8,580,953 B2  Page 1 of 1
APPLICATION NO. : 11/570849
DATED : November 19, 2013
INVENTOR(S) : Markus Frank et al.

It is certified that error appears in the above-identified patent and that said Letters Patent is hereby corrected as shown below:

Title Page, Item (75), correct the listing of the *Inventors* with the following:

-- Markus Frank, Baden-Baden (DE); Frank Loeker, Krefeld (DE); Dirk Paepen, Geldern (DE); Scott Smith, Greensboro, NC (US) --.

In the Specification

Column 7,
Line 40, "$M_{n+2}{}^I[P_n$" should read -- $M^I_{n+2}[P_n$ --.

Line 41, "$M_n{}^I[H_2P_nO_{3n+1}]$" should read -- $M^I_n[H_2P_nO_{3n+1}]$ --.

Line 42, "$M_n{}^I[H_2P_nO_{3n+1}]$" should read -- $M^I_n[H_2P_nO_{3n+1}]$ --.

In the Claims

Column 25, Claim 8,
Line 45, "$M_{n+2}{}^I$" should read -- $M^I_{n+2}$ --.

Line 46, "$M_n{}^I[H_2P_nO_{3n+1}]$" should read -- $M^I_n[H_2P_nO_{3n+1}]$ --.

Signed and Sealed this
Fourth Day of February, 2014

Michelle K. Lee
*Deputy Director of the United States Patent and Trademark Office*